(12) United States Patent
Schuler et al.

(10) Patent No.: US 9,115,392 B2
(45) Date of Patent: *Aug. 25, 2015

(54) METHOD FOR DETECTING GENE MODIFICATIONS BY MEANS OF ASYMMETRICAL PCR AND BLOCKING AGENTS

(75) Inventors: Martin Schuler, Essen (DE); Frank Breitenbuecher, Muelheim an der Ruhr (DE); Sandra Hoffarth, Muelheim an der Ruhr (DE); Sarah-Luise Stergar, Gelsenkirchen (DE)

(73) Assignee: UNIVERSITAET DUISBURG-ESSEN, Essen (DE)

( * ) Notice: Subject to any disclaimer, the term of this patent is extended or adjusted under 35 U.S.C. 154(b) by 253 days.

This patent is subject to a terminal disclaimer.

(21) Appl. No.: 13/498,699

(22) PCT Filed: Sep. 9, 2010

(86) PCT No.: PCT/EP2010/005532
§ 371 (c)(1),
(2), (4) Date: Jun. 5, 2012

(87) PCT Pub. No.: WO2011/042104
PCT Pub. Date: Apr. 14, 2011

(65) Prior Publication Data
US 2012/0244538 A1 Sep. 27, 2012

(30) Foreign Application Priority Data

Oct. 9, 2009 (DE) .......... 10 2009 049 001
Mar. 15, 2010 (DE) .......... 10 2010 011 533
Jun. 29, 2010 (DE) .......... 10 2010 025 496

(51) Int. Cl.
*C12Q 1/68* (2006.01)
*C12P 19/34* (2006.01)

(52) U.S. Cl.
CPC .......... *C12Q 1/6827* (2013.01); *C12P 19/34* (2013.01); *C12Q 1/68* (2013.01); *C12Q 1/6858* (2013.01); *C12Q 1/6886* (2013.01); *C12Q 2600/156* (2013.01)

(58) Field of Classification Search
CPC .................... C12Q 1/68; C12P 19/34
USPC .................................. 435/6.1, 91.2
See application file for complete search history.

(56) References Cited

U.S. PATENT DOCUMENTS

| | | | |
|---|---|---|---|
| 6,110,676 A * | 8/2000 | Coull et al. .......... | 435/6.18 |
| 7,332,277 B2 * | 2/2008 | Dhallan .......... | 435/6.16 |
| 2003/0134307 A1 * | 7/2003 | Beckman et al. .......... | 435/6 |
| 2010/0009360 A1 | 1/2010 | Rosell Costa et al. | |

FOREIGN PATENT DOCUMENTS

WO WO 2008/009740 A1 1/2008

OTHER PUBLICATIONS

S. Hoffarth et al.: "Hochsensitiver Nachweis von Mutationen des humanen EGF-Rezeptors bei Patienten mit nicht-kleinzelligem Lungenkarzinom", MTA Dialog, vol. 11, No. 1, pp. 26-29 (Jan. 2010).
Y. Nagai et al.: "Genetic Heterogeneity of the Epidermal Growth Factor Receptor in Non-Small Cell Lung Cancer Cell Lines Revealed by a Rapid and Sensitive Detection System, the Peptide Nucleic Acid-Locked Nucleic Acid PCR Clamp", Cancer Research, AACR, US, vol. 65, No. 16, pp. 7276-7282 (Aug. 15, 2005).
K.-A. Kreuzer et al.: "Preexistence and evolution of imatinib mesylate-resistant clones in chronic myelogenous leukemia detected by a PNA-based PCR clamping technique", Annals of Hematology, vol. 82, No. 5, pp. 284-289 (Apr. 12, 2003).
A. Senescau et al.: "Use of a Locked-Nucleic-Acid Oligomer in the Clamped-Probe Assay for Detection of a Minority Pfcrt K76T Mutant Population of Plasmodium falciparum", Journal of Clinical Microbiology, vol. 43, No. 7, pp. 3304-3308 (Jul. 2005).
Y. Kawai et al.: "Sensitive detection of EGFR mutations using a competitive probe to suppress background in the SMart Amplification Process", Biologicals, Academic Press Ltd., vol. 36, No. 4, pp. 234-238 (2008).
C. Willmore-Payne et al.: "The Use of EGFR Exon 19 and 21 Unlabeled DNA Probes to Screen for Activating Mutations in Non-Small Cell Lung Cancer", Journal of Biomolecular Techniques, vol. 19, No. 3, pp. 217-224 (2008).
M. Erali et al.: "High Resolution Melting Applications for Clinical Laboratory Medicine", Experimental and Molecular Pathology, vol. 85, No. 1, pp. 50-58 (Aug. 2008).
H. Asano et al.: "Detection of EGFR Gene Mutation in Lung Cancer by Mutant-Enriched Polymerase Chain Reaction Assay", Clinical Cancer Research, vol. 12, No. 1, pp. 43-48 (Jan. 1, 2006).
H. Kimura et al.: "Detection of Epidermal Growth Factor Receptor Mutations in Serum as a Predictor of the Response to Gefitinib in Patients with Non-Small-Cell Lung Cancer", Clinical Cancer Research, vol. 12, No. 13, pp. 3915-3921 (Jul. 1, 2006).
W. Pao et al.: "Epidermal Growth Factor Receptor Mutation Testing in Lung Cancer: Searching for the Ideal Method", Clinical Cancer Research, vol. 13, No. 17, pp. 4954-4955 (Sep. 1, 2007).
Y. Yatabe et al.: "Epidermal growth factor receptor mutations in lung cancers", Pathology International, vol. 57, No. 5, pp. 233-244 (2007).
S. V. Sharma et al.: "Epidermal growth factor receptor mutations in lung cancer", Nature Reviews, Cancer, vol. 7, pp. 169-181 (Mar. 2007).
F. Hoffmann-La Roche Ltd.: "LightCycler® 480 Probes Master", Data Sheet, pp. 1-18 (Feb. 2008).
Invitrogen Corp.: "PureLink™ Genomic DNA Kits", Data Sheet, pp. 1-36 (Feb. 13, 2007).

* cited by examiner

*Primary Examiner* — Ardin Marschel
(74) *Attorney, Agent, or Firm* — Norman B. Thot

(57) ABSTRACT

A method of detecting at least one gene modification such as a mutation in a gene includes carrying out an asymmetric polymerase chain reaction (PCR) with a combined use of at least one detectable mutation-specific hybridization probe (sensor probe) and at least one wild-type specific blocking agent which inhibits a binding of the at least one detectable mutation-specific hybridization probe (sensor probe) to a wild-type gene so as to provide at least one of a selective intensification and an amplification of a detection of a gene segment of a mutation gene having a gene modification.

26 Claims, 7 Drawing Sheets

METHOD FOR DETECTING GENE MODIFICATIONS BY MEANS OF ASYMMETRICAL PCR AND BLOCKING AGENTS

CROSS REFERENCE TO PRIOR APPLICATIONS

This application is a U.S. National Phase application under 35 U.S.C. §371 of International Application No. PCT/EP2010/005532, filed on Sep. 9, 2010 and which claims benefit to German Patent Application No. 10 2009 049 001.9, filed on Oct. 9, 2009, to German Patent Application No. 10 2010 011 533.9, filed on Mar. 15, 2010, and to German Patent Application No. 10 2010 025 496.7, filed on Jun. 29, 2010. The International Application was published in German on Apr. 14, 2011 as WO 2011/042104 A1 under PCT Article 21(2).

FIELD

The present invention relates to the area of detection of gene modifications, especially mutations, in genomic DNA, wherein the gene modification or mutation is connected in particular with an oncosis and/or cancer, such as a bronchial carcinoma. Based on detection of the gene modification, therapeutic approaches or measures for targeted treatment of the cancer or oncosis can be appropriately optimized.

The present invention in particular provides a method of detecting at least one gene modification, in particular a mutation, in a gene, for example, in a gene coding, for a protein connected with an oncosis and/or cancer.

The present invention also relates to a composition, in particular for use in the context of an asymmetric polymerase chain reaction, which has specific components, wherein the composition according to the present invention can be ready for use, for example, in the form of an aqueous solution or dispersion or else in the form of components spatially separated from one another, based on a kit or kit-of-parts.

The present invention finally relates to the use of the composition according to the present invention for detecting at least one gene modification, in particular a mutation.

SEQUENCE LISTING

The Sequence Listing associated with this application is filed in electronic form via EFS-Web and is hereby incorporated by reference into this specification in its entirety. The name of the text file containing the Sequence Listing is Sequence_Listing_II_16_MAY_2012. The size of the text file is 14,489 Bytes, and the text file was created on May 16, 2012.

BACKGROUND

Cancers or oncoses are, after cardiovascular diseases, the second most common cause of death in Germany. If therapy is started in good time or the oncosis occurs late in life and then only progresses slowly, not every cancer proves fatal. The current rate of cure for all cancers averages 30 to 40%, but there are marked variations depending on the actual cancer. For example, cancers of the respiratory tract, especially lung cancer, are among the poorly treatable cancers.

In cancers or in tumor cells, the coordination of growth, division and destruction or apoptosis in the cell cluster is disturbed or disabled. Often endogenous regulatory signals are not recognized or are not executed or are executed incorrectly, which is often linked causally to genetic defects or gene modifications, such as mutations. Genetic changes, such as mutations, can thus lead to changes in the structure and in the physiology of proteins encoded by the affected genes, which may induce or promote tumor growth. The development of cancer, or carcinogenesis, in particular the primary disease event, may thus be due to a change of the genetic material, which cannot be compensated by endogenous monitoring and correcting systems and consequently, for example, in the context of cell division processes, can be transmitted to succeeding cells, which sometimes leads to the development of a primary tumor.

Lung carcinomas, which are also designated with synonyms such as bronchial carcinomas, bronchogenic carcinoma or lung cancer, constitute a malignant oncosis based on degenerated cells in particular of the bronchi or bronchioles. Bronchial or lung cancer is one of the commonest malignant cancers in humans and represents one of the commonest causes of death due to cancer in the Western Hemisphere. The number of new cases of lung cancer in Germany is about 50,000 persons per year. The main cause of lung cancers is inhalation of cigarette smoke. In addition, there are some toxic substances, such as asbestos or chromium, that can also induce lung carcinomas. Owing to the sometimes completely absent or only nonspecific symptoms in the early stages of the disease, most first diagnoses of lung cancer are not made until the later stages of the disease, so that one of the most promising treatment options—complete surgical removal of the tumor—is often no longer possible, in particular also because metastasis has already begun. The rate of cure of bronchial carcinoma is generally very poor and a five-year survival rate is below 10%; the probability of survival after two years is less than 20%.

About a quarter of all malignant tumors or malignant neoplasms are bronchial carcinomas. In men, bronchial carcinoma is globally the commonest oncosis, in Germany it is the third-commonest after prostate cancer and colorectal carcinoma, but bronchial carcinoma is in first place as the cause of cancer deaths.

Based on their histology and the disease course, lung cancers are generally divided into two groups, namely small-cell lung cancer (SCLC) on the one hand and non-small-cell lung cancer (NSCLC) on the other hand. Non-small-cell lung cancer or NSCLC represents the largest group of bronchial carcinomas, with an incidence of 85% of lung cancers. Depending on the histological findings, non-small-cell lung cancer or NSCLC may be differentiated into a sometimes fusiform squamous cell carcinoma, an adenocarcinoma and a large-cell carcinoma or giant-cell carcinoma.

Regarding the therapeutic approaches known in the prior art for the treatment of lung cancer, in particular small-cell lung cancer, these focus primarily on a therapeutic approach based on chemotherapy or radiotherapy. However, therapies of this kind are associated with severe side-effects and often do not lead to the desired therapeutic success. In studies, even platinum-based combination therapies only achieve a median survival increase of just 10 to 12 months. Recently, patients with a diagnosis of small-cell lung cancer or NSCLC have been offered alternative therapies to the usual treatment with chemotherapeutics. Drugs are thus used which, in contrast to cytostatics, act specifically on tumor cells, and accordingly also have far fewer side effects. These include in particular the substances available under the international nonproprietary names gefitinib, erlotinib and cetuximab, which specifically bind to or inactivate the receptor of the epidermal growth factor (EGF) often involved in lung cancers, namely the so-called EGF receptor or EGFR.

The EGF receptor (epidermal growth factor receptor) is a member of the so-called ErbB family with a subfamily of four closely-related receptor tyrosine kinases. The EGF receptor is often also designated synonymously as HER1, EGFR1 or ErbB-1.

The EGF receptor is a transmembrane receptor with intrinsic tyrosine kinase activity, which occurs in all cell types. The receptor has a membrane channel and in the cytoplasmic portion it has a kinase domain with ATP binding site. The EGF receptor is classified among the growth factor receptors.

In non-malignant cells, after binding of its ligand (EGF), the receptor is activated by dimerization and phosphorylation and consequently conveys growth and survival signals into the interior of the cell. Activation of the receptor finally leads to stimulation of cell growth and prevention of apoptosis or programmed cell death. The EGF receptor supports proliferation and cell survival.

However, overexpression and/or certain mutations in the EGF receptor, such as are sometimes observed in tumor cells, bring about permanent or excessive activation of the receptor, which is accompanied by an undesirable level of cell growth, excessive cell division and therefore tumor formation or tumor growth. For malignant cells, constant imparting of growth signals is of advantage as they bring about or support the accelerated proliferation and survival of the malignant cells. Tumor cells that possess overexpression or activating mutations with respect to the EGF receptor are even dependent on the permanent or excessive activation of the EGF receptor for their proliferation and their survival. In various types of tumors, the EGF receptor is therefore up-regulated or is in a mutated form, which has the result that the tumor cells in question grow uncontrollably and multiply. The aforementioned active substances aim to block the oncogenic signal of the EGF receptor and thus stop or slow down tumor growth.

The EGF receptor may thus be directly linked to an oncosis or cancer, in particular a lung or bronchial carcinoma, such as small-cell lung cancer, especially as, in its mutated form, the EGF receptor leads to uncontrolled growth and multiplication of tumor cells. Specific blocking or inactivation of the, in particular mutated, EGF receptor can, therefore, lead to restriction or stopping of growth of tumor cells.

In the context of the present invention, it is important that through targeted inhibition of the EGF receptor, the activation of the receptor can be reduced or inhibited. Over 80% of the mutations of the EGF receptor in patients with small-cell lung cancer or NSCLC are based on various deletions in exon 19 of the EGF receptor and on a point mutation in exon 21, namely the so-called L858R mutation (i.e., exchange of the amino acid leucine L at position 858 in the amino acid sequence of the EGF receptor for the amino acid arginine R). Patients with a lung tumor who have one of these changes are especially suitable for therapy with EGF receptor inhibitors. In particular, the drugs or substances gefitinib and erlotinib have high specificity of action with respect to EGF receptors that have said mutations. Therapy with specific inhibitors of the EGF receptor, especially with respect to its mutated form, is generally well-tolerated and also displays a certain efficacy. Owing to the high specificity, the mutation-bearing receptors are inhibited selectively, which reduces side-effects and increases the therapeutic effect.

After a certain time, most patients develop a so-called secondary mutation, which arises in addition to the mutation already present and leads to resistance to erlotinib and gefitinib. In roughly 65% of these cases, a mutation is found in exon 20 of the EGF receptor, which is a T790M mutation (i.e., exchange of the amino acid threonine T for methionine M at position 790 of the EGF receptor). For these patients, drugs are available whose mechanism of action and specificity differ from the drugs of the so-called first generation, such as erlotinib and gefitinib. The inhibitors of the so-called second generation bind in particular irreversibly to the receptor, and not reversibly, as is the case with the aforementioned first-generation drugs. Patients with small-cell lung cancer, who, owing to the secondary mutation, in particular the T790M mutation, no longer respond to first-generation drugs, can therefore continue treatment with a second-generation EGF receptor inhibitor. These inhibitors are also highly specific and effective so that the growth and survival of the tumor cells can be slowed or prevented.

Against this technical and medical background, a rapid, easily managed mutation analysis that leads to exact results with respect to the EGF receptor in patients with lung cancer is therefore extremely important, in particular also against the background of tuning or optimizing the therapy with respect to the specific mutation finding.

In particular, to provide an optimum therapeutic approach by means of highly effective, individualized medicine, it is necessary to investigate the tumor tissue for the status of the EGF receptor, especially with respect to mutations that may be present, in particular as described above. On this basis, these patients can be treated with the corresponding EGF receptor inhibitors according to their mutation status.

Based on a highly informative mutation analysis with respect to the EGF receptor, it is then possible to carry out appropriate targeted therapy with the respective drugs.

Various methods or approaches based on molecular biology are available in the prior art for detecting mutations in genomic DNA from tumor tissue. For example, sequencing according to Sanger is used routinely. However, this method has the disadvantage that mutations can only be detected when the DNA bearing them is present at a level of at least 20% to 25% in the sample to be analyzed relative to the total DNA content of the sample. The expenditure of time for execution and evaluation is moreover relatively high, as the test can take several hours.

Another method of the prior art for the analysis of mutations is the so-called polymerase chain reaction (PCR), for example, so-called real-time PCR or RT-PCR. The analysis time can be reduced using this method. Moreover, execution is relatively economical and the sensitivity with respect to the mutation to be detected or analyzed is already higher. The results obtained with conventional PCR are nevertheless not always satisfactory, especially if the sample only has extremely small amounts of mutation material. As a result, conventional PCR only has a low level of sensitivity.

SUMMARY

An aspect of the present invention is to provide a method of detecting gene modifications, especially mutations, which at least partially avoids or else at least lessens the aforementioned disadvantages of the prior art.

In particular, a method is to be provided that has very high sensitivity, i.e., leads to highly informative results even with very small amounts of mutation material in a sample or material to be analyzed.

It should moreover be possible to use the method according to the present invention on a large number of various kinds of samples or materials from patients, for example, blood samples, lymph, cells, purified DNA or the like.

The method according to the present invention should moreover provide well-founded evidence with respect to a "mutation-dependent" or "mutation-specific" therapeutic approach, and thus optimize the basic treatment regimen, in particular with respect to the selection of special drugs.

The method proposed according to the present invention should in particular be suitable for the detection or analysis of mutations in proteins, in particular, the EGF receptor, wherein the mutation or the protein with the mutation is linked to the development or the occurrence of lung cancers, in particular of small-cell lung cancer or NSCLC.

In an embodiment, the present invention provides a method of detecting at least one gene modification such as a mutation in a gene which includes carrying out an asymmetric polymerase chain reaction (PCR) with a combined use of at least one detectable mutation-specific hybridization probe (sensor probe) and at least one wild-type specific blocking agent which inhibits a binding of the at least one detectable mutation-specific hybridization probe (sensor probe) to a wild-type gene so as to provide at least one of a selective intensification and an amplification of a detection of a gene segment of a mutation gene having a gene modification.

In an embodiment, the present invention provides a composition for use in an asymmetric polymerase chain reaction (PCR), such as to detect at least one gene modification such as a mutation in a gene, which comprises a detectable mutation-specific hybridization probe (sensor probe). A first primer which binds at least substantially specifically to a single-stranded DNA of the mutation gene (probe strand), with which the detectable mutation-specific hybridization probe (sensor probe) can interact. A second primer which can interact at least substantially specifically with a single-stranded DNA of the mutation gene complementary to the probe strand (complementary strand). A wild-type specific blocking agent which inhibits a binding of the detectable mutation-specific hybridization probe (sensor probe) to the wild-type gene. A content of the first primer in the composition is greater than a content of the second primer.

In an embodiment, the present invention provides a method of using the composition to detect at least one gene modification, such as a mutation, in a gene, includes providing the composition and detecting at least one gene modification with the composition.

Embodiments, implementations, advantages and the like, which for purposes of avoiding repetitions are only presented for one aspect of the present invention, of course also apply correspondingly with regard to the other aspects of the present invention.

BRIEF DESCRIPTION OF THE DRAWINGS

The present invention is described in greater detail below on the basis of embodiments and of the drawings in which.

DETAILED DESCRIPTION

Figure 1:
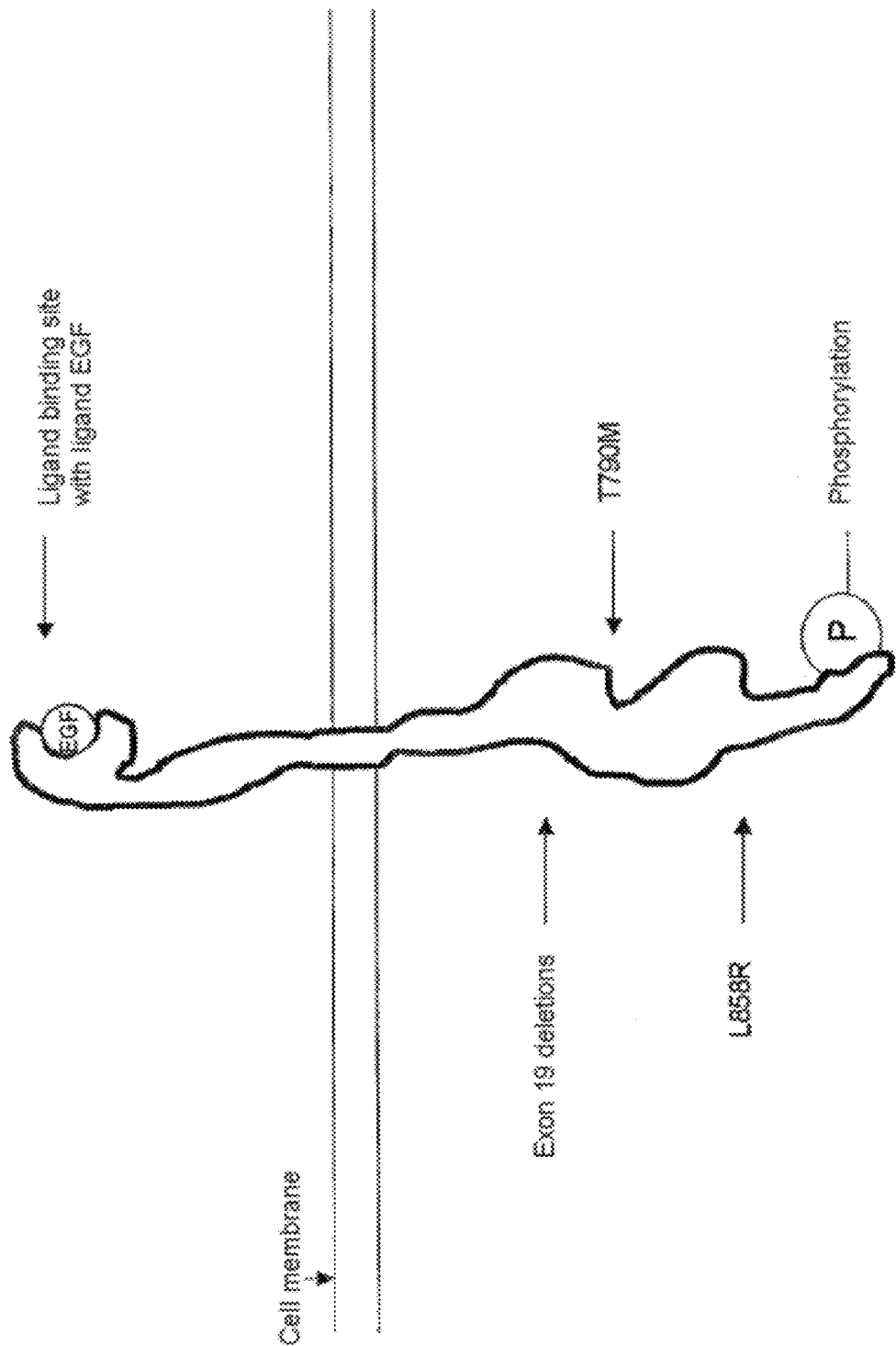
FIG. 1 shows a schematic structure of the EGF receptor with the corresponding localization of the mutations.

In an embodiment, the present invention provides a method of detecting at least one gene modification, in particular mutation, in a gene, for example, in a gene coding for a protein connected with an oncosis and/or cancer, in particular wherein the gene having the gene modification (=mutated gene) or the allele having the gene modification (=mutated allele)—also called synonymously mutation gene or mutation allele respectively—is present together with other genes or alleles coding for the protein, but not having a gene modification (=wild-type genes or wild-type alleles), wherein the method according to the present invention is characterized in that the method is carried out by means of asymmetric polymerase chain reaction (PCR) in combination with the use of at least one detectable mutation-specific hybridization probe (sensor probe) on the one hand and at least one wild-type specific blocking agent (=clamp) inhibiting the binding of the sensor probe to the wild-type gene or wild-type allele, in particular so that there is selective intensification and/or amplification of detection with respect to a gene segment or segment, in particular DNA segment, of the mutation gene or mutation allele having the gene modification.

The fundamental idea of the present invention is therefore that, based on the specific conception of the method according to the present invention, gene modifications or mutations in a sample or an ensemble of genes can be detected with very high sensitivity, so that even extremely small amounts of mutated DNA (=mt-DNA) can be analyzed, in particular in a mixture or ensemble with wild-type DNA or DNA that does not have a mutation (=wt-DNA). In the context of the present invention, it has therefore been possible for even small amounts or contents of DNA that have the gene modification or mutation to be analyzed very reliably in a sample and in particular even to the extent that concrete determination or special detection of particular mutations can be achieved.

In this connection, it is possible according to the present invention to detect even small amounts of mutated DNA starting from a content of about 0.0025% in a mixture with other DNA or non-mutated DNA or wild-type DNA, relative to the DNA content.

In this connection, the fundamental idea of the present invention is to increase or improve the efficacy or sensitivity of the method by appropriate execution of an asymmetric polymerase chain reaction, in which there is, primarily or selectively, an intensification or amplification of the single-stranded DNA of the mutation gene, which has the mutation and to which the sensor probe, serving for the actual detection in the sense of instrumental detection, binds specifically. This can, for example, as described in more detail hereunder, be carried out by using different amounts of primers, which are also designated synonymously as (PCR) starter molecules, wherein in the context of the present invention, in particular the amount of the primer that binds to the so-called probe strand with the mutation is increased. As a result, according to the present invention, the amount of single-stranded DNA with the mutation, in whose region the sensor probe binds specifically, is increased compared to the other single-strands of DNA, so that in the sample, the DNA strand to which the sensor probe hybridizes specifically is as it were overrepresented and therefore owing to the statistically more frequent binding of the sensor probe, an amplified sensor signal is the result.

In the context of the present invention, it was moreover possible, as a complete surprise, to increase the sensitivity even further, on the one hand by using a mutation-specific hybridization probe or sensor probe that has an increased binding affinity or specificity or selectivity to the mutation site or the mutation region in the mutated DNA strand or DNA single-strand compared to the corresponding wild-type DNA single-strand—i.e., to the original single strand without mutation. On the other hand, in the context of the method according to the present invention, the asymmetric polymerase chain reaction is moreover carried out in the presence of a special blocking agent or blocker, which in fact binds specifically, i.e., with increased affinity, to the DNA single-strand without mutation or the wild-type DNA single-strand in the segment corresponding to the mutation region and therefore prevents or decreases nonspecific binding of the sensor probe in this region of the non-mutated DNA.

Based on this "ternary" combination of measures, in the context of the present invention, it was possible, as a complete surprise, to provide a method of detecting mutations or gene modifications that leads to a labeled amplification, especially of the measuring signal attributable to the mutation to be investigated, in the sense of discrimination or intensification relative to the other signals in the sample, so that on the basis of the method according to the present invention, even very small amounts of mutated DNA in a sample or starting material can be analyzed. Based on the highly sensitive method, in the context of the present invention, it is possible to make use of samples that have only small amounts of DNA derived from tumor cells. Therefore, in the context of the present invention, even extremely small proportions of mutated DNA can be detected, without the need to perform biopsies, which are expensive and are sometimes problematic from the medical standpoint. Basically, however, according to the present invention, it is also possible for cell samples or cellular material, e.g., tumor cells as such, to be taken as the basis for the method according to the present invention.

Based on the method according to the present invention, with the highly informative detection or analysis of mutations, it is possible, in a targeted way, to obtain information about the state of a disease or to provide monitoring, in particular with respect to the effects of drugs or the like, and moreover, tumor therapies optimized for the concrete mutation analysis can be carried out, for example, using specific inhibitors or targeted drugs.

As noted above, in the context of the present invention, it is possible that the mutated gene (also called synonymously mutation gene) or the mutated genes (also called synonymously mutation genes) can be present as it were in an ensemble or a sample together with a wild-type gene or with wild-type genes, which is, for example, the case when both tumor cells and non-degenerated cells are present in a (starting) sample that is provided.

In the context of the present invention, it is also possible that the corresponding genes have mutation alleles and wild-type alleles or consist of these. Thus, for example, the mutation gene can, in the sense of homozygous expression, have two mutation alleles, i.e., both alleles of the gene are carriers of the corresponding gene modification or mutation. It may equally be possible that the mutation gene is of heterozygous form, and in this case an allele, namely, the mutation allele, with the gene modification or mutation and—corresponding to this—a wild-type allele without mutation relative to the mutation gene, are present. Relative to the wild-type gene, which in particular originates from healthy or non-malignant cells, both alleles are present in particular in the wild-type form or as wild-type alleles. To that extent, in the following the terms "mutation gene" or "wild-type gene" used also refer in particular to the corresponding alleles, as defined above. The method according to the present invention is therefore also suitable for detecting mutations in the respective alleles of a gene.

Furthermore, with respect to the present invention, the oncosis or cancer can be a lung cancer, in particular a non-small-cell lung cancer (NSCLC) and/or a small-cell lung cancer (SCLC), for example, a non-small-cell lung cancer (NSCLC).

In other words the present invention focuses on detecting mutations that are associated with the aforementioned cancers, in particular with non-small-cell lung cancer, or cause these diseases, for example, owing to abnormal function of the resultant gene product of the mutation gene. The present invention is not, however, limited to the aforementioned diseases. The method according to the present invention can rather be used universally for the analysis or detection of in particular known mutations or gene modifications that are associated with diseases of the organism as such. This can be achieved, for example, by specific adaptation of the mutation-specific hybridization probes or of the sensor probes, of the primers and/or of the blocking agent, so that the method according to the present invention can as it were be tailored to a large number of specific diseases.

The protein in question, modification of which can be determined by the detection or analysis of the mutation of the gene coding for the protein, is according to an embodiment of the present invention, an in particular human protein and/or a protein regulating and/or inducing cell growth and/or cellular proliferation. The protein can moreover be an in particular transmembrane receptor for growth factors, in particular with intrinsic tyrosine kinase activity. For example, the protein in question, which is associated with an oncosis or cancer, is the epidermal growth factor receptor (EGF receptor), in particular as described above. In the context of the present invention, it is in particular the human EGF receptor.

The present invention equally also comprises proteins of identical or similar structure with action that is identical or similar to the aforementioned EGF receptor. The term "EGF receptor", as used in the context of the present invention, in particular also comprises functionally identical or functionally similar variants as well as mutated forms of the EGF receptor not directly linked per se to cancer or oncosis. In particular, the term "EGF receptor" also comprises in particular at least essentially functionally similar or functionally identical isoforms and/or precursors. According to an embodiment of the present invention, the protein in question is the EGF receptor according to the locus or according to the reference number NP_005219.2 and/or in particular according to sequence listing I and/or sequence listing II. In general, the present invention also comprises functional analogues and/or isoforms of the EGF receptor in question or such forms of the EGF receptor or proteins in general that have a match in the amino acid sequence of at least 90%, in particular at least 95%, for example, at least 98%, for example, at least 99%, relative to the amino acid sequence of the EGF receptor according to sequence listing I and/or according to sequence listing II.

Sequence listing I and sequence listing II refer to the amino acid sequence of the EGF receptor. Moreover, sequence listing I is synonymous or identical in content to sequence listing II with respect to the amino acid sequence. The essential difference between the sequence listings is that sequence listing I is based on a scientifically standardized statement or representation, whereas sequence listing II was prepared on the basis of a standardized statement or representation under patent law using the software PatentIn Version 3.3. Thus, with reference to the amino acid sequence, the difference is purely formal in connection with representation, but not with respect to content.

The gene modification, in particular mutation, to be investigated or to be analyzed in the context of the method according to the present invention can therefore lead to an increased and/or excessive activity of the protein encoded by the corresponding gene and/or can be connected with this. The gene modification or mutation can therefore lead to increased or excessive cell growth and/or to increased or excessive cellular proliferation or can be connected with this. The gene modification to be investigated can lead to an activity of the protein encoded by the corresponding gene, in particular of the EGF receptor, that is pathological or deviates from the physiological norm. In other words, the gene modification, in particular mutation, brings about a change in the corresponding gene product, which is associated with the oncosis or cancer. The disease that is associated with the gene modification is, in particular, as already mentioned, a bronchial carcinoma, in particular NSCLC.

The gene modification to be detected or to be analyzed can, for example, be a point mutation and/or a frameshift mutation and/or a deletion. In an embodiment of the method according to the present invention, the gene modification is a point mutation, in particular in which individual bases at specific sites of the gene or DNA strand are exchanged or altered.

For example, the gene modification can be of such a kind that it leads to at least one deletion in exon 19 of the EGF receptor and/or is associated with this. In an embodiment of the present invention, the gene modification is a mutation, in particular a point mutation, which leads to an exchange of at least one amino acid in exon 20 and/or exon 21 of the EGF receptor as corresponding gene product or is associated with this. In this respect, the gene modification can lead to an exchange of serine at position 768 of the EGF receptor in particular for isoleucine (S768I) or can be connected with this. In the context of the present invention, however, the gene modification is, for example, one that leads to an exchange of threonine at position 790 of the EGF receptor, in particular for methionine (T790M), or is associated with this or a gene modification that leads to an exchange of leucine at position 858 of the EGF receptor, in particular for arginine (L858R), or is associated with this.

The present invention therefore aims primarily at detection or analysis or investigation of the presence of the point mutations L858R and/or T790M. T790M is a mutation in exon 20 of the EGF receptor, whereas L858R is a mutation in exon 21 of the EGF receptor. As already mentioned, said mutations L858R and T790M of the EGF receptor are specific mutations, which are linked to the induction or formation or progression of lung cancers, in particular non-small-cell lung cancer (NSCLC), and in this respect represent a target for specific drugs, as already mentioned.

The present invention is not, however, limited to the detection or analysis of the aforementioned special mutations of the EGF receptor. The method according to the present invention can rather be used with reference to a large number of mutations, especially if the mutations to be detected or to be analyzed are associated with the formation or the presence of an oncosis or cancer, in particular a bronchial carcinoma, such as small-cell lung cancer. A person skilled in the art is always capable of selecting the specific components for the mutations to be investigated in each case, such as primers, the probes that are described further hereunder and/or the blocking agent, and using them in the context of the method according to the present invention.

As already mentioned, it can be envisaged according to the present invention that the mutation gene or the mutation genes on the one hand and the wild-type gene or the wild-type genes on the other hand are present in a sample and/or an ensemble, wherein in particular the sample and/or the ensemble provided originates from a patient and/or in particular wherein the sample and/or the ensemble originates from, or can be obtained from, a body material, in particular a body fluid, for example, blood and/or tissue fluid and/or lymph and/or urine in particular with cellular constituents. Moreover, it is also possible to use prepared cellular material or tumor material, for example, based on a biopsy.

In general, the sample on which the method according to the present invention is based can be of such a kind that it has both healthy or non-malignant cells with intact EGF receptor and the relevant coding wild-type genes, and tumor cells with optionally mutated EGF receptor and the associated mutation genes or mutation alleles. For example, the sample can be one that has, along with normal or non-degenerated cells, also circulating tumor cells.

The sample or the starting material can moreover be further purified before carrying out the method according to the present invention or the DNA can be isolated from the sample for further use or can be concentrated or purified. The respective methods are sufficiently familiar to a person skilled in the art so that no further details are required.

In the context of the present invention, it is possible that gene modifications or mutations can be determined on the basis of a sample that has fewer than 1000, in particular fewer than 500, for example, fewer than 200, for example, fewer than 100 tumor cells, per ml of sample. The method according to the present invention can be carried out on the basis of samples or starting materials with DNA that have less than 1%, in particular less than 0.1%, for example, less than 0.01%, for example, less than 0.001% of tumor cells, relative to the total cell content of the sample.

The method according to the present invention can be applied with reference to a sample or a starting material that has less than 1% of mutated DNA, in particular about 0.5%, for example, about 0.05%, for example, about 0.005%, for example, about 0.0005% of mutated DNA, relative to the total DNA in the sample or in the starting material. The method according to the present invention is thus a highly sensitive and efficient method in which even the smallest traces of DNA can be analyzed to obtain information regarding the presence of mutations.

In the context of the present invention, it can moreover be envisaged that asymmetric PCR is carried out in the presence of primers, in particular in the form of oligonucleotides.

In this connection, the primers can be selected so that, in particular in the context of PCR, the gene segment of the mutation gene or mutation allele having the gene modification is amplified and/or so that the gene segment of the wild-type gene or of the wild-type allele corresponding to the gene segment of the mutation gene having the gene modification is amplified. The formulation "the gene segment of the wild-type gene corresponding to the gene segment of the mutation gene having the gene modification" is in particular to be understood as meaning the segment of the wild-type gene or wild-type allele, for which no mutation is present as such, corresponding to the segment with the mutation.

Selecting the primers permits targeted amplification or multiplication of the relevant gene segment for investigation or genetic analysis or of the corresponding gene segment of the wild-type gene and therefore discrimination against the other genes or the other DNA in the sample. In particular, the DNA to be amplified is the gene of the EGF receptor described above or, for example, a gene segment of the gene coding for the EGF protein, and in particular that gene segment in which the mutation may be present. The concrete selection of the primers to be used in this respect is familiar to a person skilled in the art, and a person skilled in the art is always capable of selecting and using the corresponding primers.

The primers used in the context of the present invention can be selected in such a way that the gene segment of the mutation gene having the deletion in exon 19 of the EGF receptor is amplified. It can equally be envisaged in the context of the present invention that the primers are selected in such a way that there is amplification of the gene segment of the mutation gene having the exchange of serine at position 768 of the EGF receptor in particular for isoleucine (S768I). In an embodiment of the present invention, the primers can be selected in such a way that there is amplification of the gene segment of the mutation gene having the exchange of threonine at position 790 of the EGF receptor, in particular for methionine (T790M), and/or there is amplification of the gene segment of the mutation gene having the exchange of leucine at position 858 of the EGF receptor, in particular for arginine (L858R).

Moreover, in this respect it may optionally be possible that at the same time amplification of the gene segment of the wild-type gene corresponding to the gene segment of the mutation gene having the gene modification can take place, in particular owing to the properties of the primers as such.

Regarding the gene segments to be amplified, the respective size or the number of base pairs should be selected in such a way that the sensor probe and the anchor probe optionally equally binding to the gene segment and further described below are capable of binding to the corresponding DNA single-strands of the respective gene segments.

In the context of the present invention, it can be envisaged that a first primer and a second primer different from the first primer are used. In this connection, the first primer should at least essentially bind specifically to the single-stranded DNA of the mutation gene (probe strand), to which the sensor probe is capable of binding or hybridizing or with which the sensor probe is capable of interacting. Equally, the first primer can, owing to the nature of the primers, also bind to the corresponding single-stranded DNA of the wild-type gene. Thus, the first primer is as it were a sense primer. As for the second primer, this should at least essentially bind specifically to the single-stranded DNA of the mutation gene complementary to the probe strand (complementary strand) or be capable of binding or interacting with it. The second primer is as it were a so-called antisense primer. The second primer can moreover bind to the respective corresponding single-stranded DNA of the wild-type gene.

In the case of the special detection or analysis of mutation T790M, the first and second primer should be selected so that specifically the gene segment of the mutation gene or of the corresponding wild-type gene having this mutation is amplified in PCR, which applies correspondingly to the analysis or detection of mutation L858R.

In the case of analysis or detection of mutation T790M, the first primer can have, non-limitatively, in particular the succession of bases or nucleotide sequence GACTCCGACTC-CTCCTTTATCCAATG (SEQ ID No. 2) or consist of this nucleotide sequence. In the case of the second primer, this can have or consist of, non-limitatively, the nucleotide sequence CACACACCAGTTGAGCAGGTA (SEQ ID NO. 3).

In the case of analysis or detection of mutation L858R, the first primer can have or consist of the nucleotide sequence GCTCAGAGCCTGGCATGAA (SEQ ID NO. 4); the second primer can have or consist of the nucleotide sequence CATC-CTCCCCTGCATGTGT (SEQ ID NO. 5).

The respective primers also comprise in particular those primers that have a comparable specificity or selectivity relative to the respective gene segments. However, this is known per se by a person skilled in the art, and a person skilled in the art is always capable, against the background of amplification of the corresponding gene segments, of selecting the specific primers in each case. The primers should be selected in such a way that these bind even outside the region of the mutation of the mutation gene to be analyzed or of the corresponding segments of the wild-type gene or the respective single-strands of DNA.

In the context of the present invention, the asymmetric PCR can be carried out in such a way, for example, that the single-strand of DNA, to which the sensor probe (probe strand) is capable of binding, is amplified more strongly or more frequently than the complementary single-stranded DNA (complementary strand), so that after amplification in the PCR assay, there are more copies of the probe strand compared to the complementary strand. This can happen, in the context of the present invention, according to an embodiment, for example, because the first primer and the second primer are selected in such a way that the amount and/or the concentration of the first primer, in particular relative to the PCR assay, is greater than the amount and/or concentration of the second primer, in particular so that there is increased and/or intensified amplification of the probe strand versus the complementary strand. In this way, there is intensified amplification of the probe strand versus the complementary single-strand of DNA, with the effect that the single-strand of DNA, on which the sensor probe is capable of binding, is present in a higher copy number, so that owing to the larger number of events relative to the binding between sensor probe on the one hand and the corresponding single-stranded DNA on the other hand, intensification or amplification of the mutation-specific sensor probe signal can take place.

In an embodiment of the present invention, the quantitative ratio of the first primer to the second primer (first primer: second primer), in particular in the PCR assay, can, for example, be in the range from 1000:1 to 1.05:1, in particular 100:1 to 1.5:1, for example, 10:1 to 2:1.

In an embodiment of the present invention, the number or concentration of the probe strand after execution of amplification, can, for example, be increased versus the complementary strand by a factor of at least 1.1, in particular 1.5, for example, 2, for example, 10, for example, 100.

As already mentioned, through the special ratio of the primers, with preference given to the first primer, in the context of the PCR-based amplification, primarily the single-stranded DNA of the mutation gene or of the mutation allele is amplified or multiplied, on which the sensor probe is capable of binding. In this way the sensor-probe-specific signal is additionally intensified.

Regarding the sensor probe (reporter probe) as such, this is a hybridization probe, which in particular in the context of PCR and the respective amplification steps, is capable of binding or hybridizing to the single-stranded DNA of the mutation gene or mutation allele in the region of the mutation to be analyzed or to be investigated, wherein the mutation as such should also be involved in the binding.

A principle underlying the present invention is that the sensor probe used in the form of a hybridization probe has increased selectivity or affinity with respect to the mutation region of the mutation gene or of the mutation allele or of the respective single strand versus the corresponding single-stranded DNA of the wild-type gene or wild-type allele, i.e.

versus the corresponding gene segment or nucleotide region, which the mutation to be investigated does not have. The selectivity or specificity with respect to the mutation region can, in a manner familiar to a person skilled in the art, be provided by special selection of the nucleotide sequence of the hybridization probe. In this respect, the nucleotide sequence or succession of bases should be selected in such a way that the corresponding nucleotide sequence is at least essentially complementary to the corresponding nucleotides of the mutation region together with the mutation. In this way, the increased sensitivity or affinity or binding strength of the sensor probe with respect to the mutation region is provided if the number of base pairings between sensor probe on the one hand and mutation region is greater than relative to an interaction, that is nonspecific in this respect, of the sensor probe with the corresponding gene segment of the wild-type gene without mutation. Without wishing to be bound to this theory, the higher binding affinity in particular based on the higher number of, on interaction of the sensor probe with the corresponding gene segment or single-strand of DNA, leads to a "firmer" binding or interaction, which compared to the interaction of the sensor probe with the corresponding region of the wild-type gene leads to a higher melting point, i.e., in particular to separation or dehybridization of the sensor probe from the respective single-stranded DNA only at higher temperatures.

In the context of the present invention, the sensor probe can, for example, be a nucleotide molecule, in particular a labelled oligo- or polynucleotide, labelled or, for example, provided with a detectable substance (marker), for example, with a substance detectable on interaction or binding of the sensor probe with the single-stranded DNA of the mutation gene, in particular a dye, for example, a fluorescent dye. In this connection, the sensor probe should have a size from 3 to 30 bp, in particular 5 to 25 bp, for example, 10 to 20 bp. The aforementioned size relates to the nucleotide segment of the sensor probe, which, as already mentioned, should be at least essentially complementary to the mutation region of the single-stranded DNA or probe strand of the mutation gene or mutation allele.

The sensor probe should therefore be selected in the context of the present invention in such a way that the sensor probe has a higher specificity or binding affinity or selectivity to the single-stranded DNA of the mutation gene or mutation allele (probe strand), in particular in the region of the gene modification, for example, mutation, than to the corresponding single-stranded DNA of the wild-type gene or wild-type allele or the corresponding single-stranded DNA in the form of the wild-type DNA strand and therefore the corresponding DNA wild-type strand without gene modification or mutation.

In an embodiment of the present invention, the sensor probe can be selected in such a way that the sensor probe binds, for example, specifically or preferentially or with increased selectivity or selectively to the single-stranded DNA of the mutation gene (probe strand) of the EGF receptor in the region of the gene modification or mutation. In this connection, the sensor probe should be formed at least essentially complementary to the region of the gene modification of the probe strand.

With reference to the analysis or detection of the point mutation T790M, the sensor probe can have the nucleotide or base sequence GGCATGAGCTGCATGATGAG (SEQ ID NO. 6). In the case of detection of the point mutation L858R, the sensor probe can have the nucleotide sequence GTTTG-GCCCGCCCAA (SEQ ID NO. 8). The aforementioned examples are non-limiting. Rather, a person skilled in the art is always capable of selecting specific sensor probes with respect to their nucleotide sequence or their nucleotide segment in such a way as to provide increased specificity to the corresponding gene segment with the mutation to be analyzed or to be detected in the sense of the present invention.

Moreover, regarding the sensor probe used in the context of the present invention, this can, for example, be selected in such a way that the sensor probe is able, in the case of the in particular specific interaction or binding with or to the single-stranded DNA of the mutation gene or mutation allele (probe strand) and/or in the case of the in particular nonspecific binding or interaction with or to the corresponding single-stranded DNA of the wild-type gene, to emit a detectable and/or measurable signal, in particular fluorescence signal. Moreover, the sensor probe can be selected in such a way that the sensor probe is able, in the case of an in particular heat-induced detachment of the single-stranded DNA of the mutation gene or mutation allele (probe strand) or of the corresponding single-stranded DNA of the wild-type gene, to emit a detectable or measurable signal that is at least reduced or else is different from the bound state, or no signal at all.

In other words, the sensor probe according to this embodiment can be formed in such a way that this, at least essentially only on interaction or binding or hybridization to the respective single-stranded DNA under excitation, for example, under excitation with electromagnetic radiation with a special wavelength or with a special wavelength range, emits a measurable signal, in particular fluorescence signal. Correspondingly, the non-bound sensor probe, even under excitation, should emit no signal or a reduced signal as such or else, as previously stated, a signal that is different or distinguishable from the bound state of the sensor probe. Especially with respect to the embodiment presented hereunder, the sensor probe can basically also be such that after excitation with electromagnetic radiation with a specified wavelength, independently of the binding to the wt-DNA or to the mt-DNA, it emits a signal as such, because in particular according to the embodiment hereunder, signal discrimination can take place based on energy transfer to another probe, which then supplies a distinguishable signal.

In an embodiment of the present invention, so-called FRET probes (fluorescence resonance energy transfer probes) can also be used. In this respect, for example, various dyes, in particular fluorescent dyes or fluorochromes, can be used, which are bound to the sensor probe or else to the sensor probe on the one hand and another molecule or probe, as described below, on the other hand. A signal can in this case be emitted depending on the spacing of the corresponding fluorescent dyes from one another and depending on the binding to the respective single-strand of DNA. The respective dyes or dye systems are well known as such by a person skilled in the art. In this respect—without wishing to be restricted to this theory—excitation does not as it were take place directly, but through excitation of one probe (e.g., an anchor probe), in particular of the dye of one probe (=acceptor), by the other probe (e.g., the sensor probe), in particular by the fluorophor of the other probe (=donor).

Excitation therefore takes place in particular through the transfer of energy of the excited fluorophor of one probe to the dye of the other probe, which then emits energy, in particular in the form of visible light.

In an embodiment of to the present invention, additionally to the sensor probe, at least one second hybridization probe (anchor probe) different from this can be used.

In an embodiment of the present invention, the anchor probe can be a nucleotide molecule, for example, provided with or labeled with at least one detectable substance (marker) in particular complementary to or compatible with the sensor probe, in particular a dye, for example, a fluorescent dye. The anchor probe should be an oligo- or polynucleotide or should have such a molecule or such a segment. The nucleotide segment of the anchor probe should have a size from 3 to 50 bp, in particular 5 to 45 bp, for example, 10 to 40 bp. The nucleotide sequence of the anchor probe should be selected in such a way that the anchor probe is capable of binding on the same single-stranded DNA as the sensor probe, wherein the binding of the anchor probe should take place in a region adjacent to the gene modification, in particular mutation, to be analyzed and therefore not in the immediate mutation region or the corresponding site of the wild-type DNA single-strand. According to the present invention, the binding of the anchor probe on the respective single-strand of DNA, in particular on the probe strand, should take place in such a way that the substances to be detected, in particular dyes, of the anchor probe on the one hand and of the sensor probe on the other hand are capable of interacting with one another to form a detectable signal, for example, in the form of emitted light, in particular after the manner of a FRET pair.

In this connection, it can be envisaged according to the present invention that the anchor probe is capable of binding to the same single-stranded DNA as the sensor probe, in particular wherein the anchor probe should be capable of binding at a distance of 1 to 5 bp from the sensor probe, so as to permit, in this way, interaction of the detectable substances, in particular fluorescent dyes, of the sensor probe on the one hand and of the anchor probe on the other hand once binding or interaction of both probes on the single-stranded DNA has occurred. The aforementioned distance of 1 to 5 bp corresponds to a spacing of about 1 to 10 nm. As already mentioned, in the context of the present invention the anchor probe can be formed in such a way that this is capable of binding both to the single-stranded DNA with the mutation (probe strand) and to the corresponding wild-type DNA single-strand. This also follows from the fact that the respective binding regions, in relation both to the probe strand and to the wild-type DNA single-strand in the region of the binding site of the anchor probe, have an at least substantially identical nucleotide sequence or succession of bases. Against this background, the anchor probe can bind with comparable specificity to the probe strand on the one hand and the wild-type DNA single-strand on the other hand, whereas the sensor probe binds with increased affinity or binding strength to the probe strand compared to the wild-type DNA single-strand. In the context of the present invention it is advantageous if the sensor probe on the one hand and the anchor probe on the other hand, in particular the detectable substance or marker of the sensor probe on the one hand and the detectable substance or marker of the anchor probe on the other hand, are capable of forming a FRET pair during binding of the probes.

In this connection there is a possibility of utilizing FRET for quantifying the underlying gene modification or mutation in the use of so-called LightCycler® probes, which are special hydrolysis probes, wherein various oligonucleotides, each labeled with a donor or acceptor (sensor probe and anchor probe), which bind next to one another on the target sequence (mutation region with respect to the sensor probe on the one hand and respective adjacent region relative to the anchor probe) of the gene segment to be investigated or the corresponding single-stranded DNA and thus bring the donor and the acceptor sufficiently close together for FRET. Pairs of probes of this kind can therefore be used for quantifying the underlying mutation in the context of the method according to the present invention and therefore as it were for quantifying PCR products. In the context of the present invention, it can be envisaged that, for example, the sensor probe is provided or labeled with a detectable substance, in particular fluorescent dye, in the form of a donor and the anchor probe correspondingly with a detectable substance, in particular fluorescent dye, in the form of an acceptor. The provision or labeling can also be reversed in the context of the method according to the present invention, i.e., provision of the sensor probe with an acceptor and of the anchor probe with a donor.

During binding of the sensor probe on the one hand and of the anchor probe on the other hand to the respective DNA strand—without wishing to be restricted to this theory—donor and acceptor are therefore brought spatially close together, to bring about FRET with corresponding excitation, which leads to a detectable signal. On detachment of the sensor probe or of the anchor probe with accompanying spacing apart, even on excitation, FRET does not occur, so that in this case no FRET signal is detectable. The underlying principle of FRET or of signal formation with the specific use of donor and acceptor molecules can therefore be adopted as a measure for the binding of sensor probe or anchor probe to a particular DNA segment. In this case, the fluorescence increases in proportion to the concentration of complementary DNA, i.e., the greater the number of sensor probes or anchor probes bound in the PCR assay.

The signal to be detected, which arises on interaction with the corresponding single-strand of DNA, can, for example, be measured at the end of an annealing phase of a PCR cycle. The fluorescence can moreover be determined or detected in the context of a melting curve analysis, as described below.

In the case of detection or analysis of the mutation T790M, the anchor probe can in particular have or consist of the nucleotide or base sequence CACGGTGGAGGTGAGGCAGATGC (SEQ ID NO. 7). In the case of analysis or detection of mutation L858R, the nucleotide or base sequence of the anchor probe comprises the nucleotide or base sequence GCATGGTATTCTTTCTCTTCCGCACCCAGC (SEQ ID NO. 9) or consists thereof. A person skilled in the art is always capable of correspondingly selecting or tailoring the anchor probe to be specially formed or used for detecting the respective mutation.

Another possibility for analysis or detection of the underlying gene modification or mutation utilizing FRET is the application of the sensor probe used according to the present invention in the form of a molecular beacon. Molecular beacons are oligonucleotides that are coupled or labeled both with a donor and with an acceptor. The nucleotides at the 5'-end of the probe are complementary to the nucleotides at the 3'-end, so that a loop-like secondary structure, characteristic of molecular beacons, can form. The molecular beacon can be formed in such a way that in the state designated as stem-loop there is no fluorescence. By attaching the loop region to a complementary DNA sequence, through the transposition of donor and acceptor, a change in fluorescence can be observed or detected. In general, molecular beacons are based on the so-called quencher principle. The relevant principles are familiar to a person skilled in the art, and a person skilled in the art is always capable of selecting suitable molecular beacons for use in the context of the present invention.

Furthermore, the applicant found, as a complete surprise, that the limit of detection or sensitivity of the method according to the present invention for the detection or analysis of certain mutations can be further increased significantly by carrying out the asymmetric PCR and the respective use of mutation-specific hybridization probes in a special combination with the use of at least one blocking agent. As a complete surprise, this can result in a further increase in sensitivity, wherein the totality of the measures envisaged according to the present invention—use of mutation-specific sensor probes, asymmetric PCR and use of special blocking agents—goes beyond the action of the individual measures, so that as a complete surprise, the measures performed according to the present invention act synergistically with respect to improvement of the sensitivity of the method according to the present invention.

In the context of the present invention, the blocking agent can, for example, be selected in such a way that the blocking agent has a higher specificity or binding affinity or selectivity with respect to the single-stranded DNA of the wild-type gene or wild-type allele, in particular with respect to the region of the single-stranded DNA of the wild-type gene or wild-type allele that corresponds to the gene segment of the mutation gene or mutation allele having the gene modification (wild-type DNA strand), versus the corresponding mutation gene or the respective single-stranded DNA with the gene modification or mutation (mutated DNA strand). In other words, the blocking agent should be selected in such a way that it binds with higher specificity or selectively on the wild-type DNA strand and in particular on the position or site corresponding to the mutated single-strand of DNA, so as to reduce or prevent the nonspecific binding of the sensor probe to the wild-type DNA strand. Blocking agent on the one hand and sensor probe on the other hand thus behave competitively with respect to the binding sites, and the binding of the sensor probe to the wild-type DNA strand is reduced or prevented. In this way, the sensor probe signal to be detected can be further discriminated or amplified relative to the mutation to be detected as fewer sensor probes bind non-specifically to the wild-type DNA strand, provided the blocking agent is present in the PCR assay. With respect to the mutated DNA strand, the sensor probe has higher affinity than the blocking agent, so that the binding of the sensor probe to the mutated DNA strand is at least essentially not influenced or prevented by the blocking agent.

In this connection, the bond and/or the complex of the blocking agent with the single-stranded DNA of the wild-type gene should have greater stability, in particular a higher melting point, than the bond or the complex of the sensor probe with the single strand of the mutation gene. This can be provided in the context of the present invention in that the nucleotide sequence of the blocking agent is at least essentially complementary to the non-mutated region of the wild-type DNA single-strand corresponding to the mutation region of the mutated DNA single-strand.

In an embodiment of the present invention, the blocking agent is selected in such a way that it has or consists of a nucleotide molecule, in particular an oligo- or polynucleotide. The blocking agent should have a size from 3 to 30 bp, in particular 5 to 25 bp, for example, 10 to 20 bp.

The blocking agent according to the present invention should be selected in such a way that the blocking agent is at least essentially complementary to the single-stranded DNA of the wild-type gene or wild-type allele, in particular to the region of the single-stranded DNA of the wild-type gene or wild-type allele, which corresponds to the gene segment of the mutation gene or mutation allele having the gene modification. The region of the wild-type DNA single-strand that corresponds to the gene segment of the mutation gene having the gene modification or to the segment of the single-stranded DNA having the mutation, therefore represents as it were the segment of the wild-type DNA strand of the wild-type gene analogous to the mutation region, on which the blocking agent or blocker is capable of binding specifically.

By using the specific blocking agent, the nonspecific binding of the sensor probe to the wild-type strand is inhibited or reduced, so that only or primarily the mutated DNA strand is multiplied in PCR and the probes used can bind to the mutated DNA without competition. The blocking agent thus prevents or reduces on the one hand the amplification of the wild-type DNA strand and on the other hand the nonspecific binding of the sensor probe to the wild-type DNA strand, in particular in the sense of competitive binding, which further improves the measurement result. In this way, it is therefore possible—without wishing to be restricted to this theory—as it were for suppression of the wt-signal to occur.

The blocking agent should therefore, for this purpose, in general be such that it has very high binding strength relative to the wild-type single-strand and only melts at very high temperatures. In this connection, the blocking agent should be selected in such a way that the blocking agent has bridged nucleic acids, in which the sugar moiety, in particular the ribose moiety, is chemically modified, in particular wherein the ribose moiety has an oxygen/methylene bridge, for example, on the $C_2$ and $C_4$ atom of the ribose moiety.

In this connection, the blocking agent can be selected in such a way that the blocking agent is a nucleic acid analogue in the form of a locked nucleic acid (LNA). These locked nucleic acids are in particular structurally less flexible and therefore rotation-stiff molecules, which bind or hybridize specifically to the DNA strand with development of an increased melting point.

In this connection, with respect to the detection or analysis of the mutation T790M, the blocking agent, in particular in the form of an LNA, should have or consist of the nucleotide sequence TGAGCTGCGTGATG (SEQ ID NO. 10); with respect to the detection or analysis of the mutation L858R, the blocking agent, in particular in the form of an LNA, should have the nucleotide sequence GCCAGCCCAAAATCT (SEQ ID NO. 11) or consist of this nucleotide sequence.

In the context of the present invention, it is equally possible for the blocking agent to be another nucleic acid analogue, in particular wherein the blocking agent has a peptide and/or peptide-based backbone and/or in particular wherein the blocking agent is a peptide nucleic acid (PNA). This is a DNA analogue in which the sugar-phosphate backbone is replaced with a pseudopeptide. Peptide nucleic acids of this kind also lead to higher affinity of binding to the complementary DNA sequence, which leads to the formation of firmer or more stable bonds, accompanied by an increase in melting point.

In an embodiment, the method according to the present invention can be carried out in such a way that for detection of the gene modification, in particular of the mutation, in particular following the polymerase chain reaction (PCR), a melting curve is recorded or a melting curve analysis is carried out. In this connection the reaction mixtures can be heated slowly, for example, up to 95° C. At the point or at the temperature at which 50% of the sensor probes have detached from the resultant PCR products, there is a marked decrease in fluorescence. If the sensor probe has bound specifically to the mutated single-strand of DNA, the dehybridization of the sensor probe takes place at a higher temperature compared to binding on the corresponding wild-type sequence or the corresponding wild-type DNA single-strand. The corresponding analysis of the melting curves therefore allows conclusions to be drawn about the presence of a specific mutation.

In particular, the melting temperature of the sensor probe, especially at the end of a PCR run, is lower in binding to wt-DNA than in binding to mt-DNA, for which the sensor probe is specific.

In this respect, the cleavage or dehybridization in particular of the sensor probe from the respective single-stranded DNA of the mutation gene or of the wild-type gene can be detected, in particular wherein detection is photometric, in particular by measurement of fluorescence. As already shown, the dehybridization or cleavage of the sensor probe from the respective single-stranded DNA leads to a decrease in fluorescence, wherein the respective melting point is lower owing to the lower binding strength or affinity with respect to the wild-type DNA single-strand than with respect to the single-stranded DNA with the corresponding mutation. By using the mutation-specific sensor probes, it can accordingly be established whether mutated gene forms are present in a sample and what mutations are actually involved. For better analysis of the melting curves, these can be represented in the form of the first mathematical derivative; in particular, the maxima of the relevant first mathematical derivative represent the respective melting points.

In the context of the method according to the present invention, the procedure to be followed can therefore be that, based on the melting point or points and/or melting point ranges of the melting curve, it can be concluded whether a gene modification, in particular a mutation, is present and in the case of presence of a mutation, the type of mutation is determined. In other words, based on the analysis or assignment (i.e., assignment via a reference, as described below) of the melting points or melting ranges, it can be established whether and, if in the affirmative, which concrete mutation is present in the sample.

In this connection, for example the procedure to be followed can be that in the context of the melting curve analysis, parallel comparative or reference assays are conducted concurrently or analyzed or alternatively these comparative or reference assays have been measured beforehand and/or independently (i.e., in other words the method is standardized by means of a reference). For example, at least one reference assay based on a wild-type DNA or a wild-type gene or allele can be conducted concurrently in an in particular parallel assay or can be measured or standardized beforehand. The reference assay can be conducted or prepared without blocking agent, i.e., another reference assay of the wild-type gene can also be conducted without blocking agent. Equally, it can be envisaged that at least one reference assay based on a gene modification or mutation to be analyzed and/or a defined or previously known gene modification or mutation is conducted concurrently in an in particular parallel assay or is measured or standardized beforehand; these may in particular be reference assays that contain mutation genes or mutation alleles based on the T790M mutation and/or based on the L858R mutation.

Comparison of the melting curves obtained with the samples to be analyzed on the one hand and the assays or measurements with the reference then makes it possible to state whether a special mutation is present in the sample (i.e., testing for the presence of a gene modification or mutation and if in the affirmative, the type of gene modification or mutation). It can generally be assumed that a gene modification or mutation is present if, relative to the reference assay with the wild type, different melting points or melting ranges, in particular at higher temperatures, are found for the sample to be investigated. The presence of a gene modification or mutation can also be concluded by comparing the melting curve with that of the respective reference assay with the relevant mutation gene, wherein the presence of at least essentially the same melting points or ranges can be taken as an indication of the presence of identical gene modifications or mutations.

In an embodiment of the present invention, it is also possible to perform the analysis for the presence of a mutation without reference assay, in particular if melting points or ranges are already known, or else if standardization is carried out beforehand (in particular as described above).

Purely as a non-limiting example, an analysis or evaluation based on testing with a parallel wild-type reference assay is described in more detail below:

Regarding analysis of the melting curves, in general the melting curve with the highest specific melting temperature or the highest melting temperature range is assigned to the mutation gene, i.e., the presence of various melting curves with different melting points or ranges can be taken as proof or an indication of the presence of a mutation, wherein the curve with the higher melting point or melting range can be ascribed to the firmer binding of the sensor probe to the mutated single-stranded DNA and therefore to the mutated form. Moreover, if there are several melting curves, the melting curve with the lower specific melting temperature or the lower melting temperature range can be assigned to the wild-type gene, wherein the respective melting curve with the lower melting temperature or the lower melting temperature range is brought about causally by the less strongly developed and nonspecific binding of the sensor probe to the non-mutated segment of the wild-type DNA single-strand. If wild-type DNA is also present in the sample to be analyzed, equally a melting point or range occurring at low temperatures can develop for the melting curve of the genetically altered or mutated form, but owing to the measures carried out according to the present invention, generally this has a smaller maximum signal (e.g., suppression of binding of the sensor probe and/or suppression of amplification).

Moreover, in the context of the present invention, in addition to the aforementioned determination or analysis of whether a mutation is present in a sample and which mutation it is, it is equally possible to obtain an indication of whether the mutation is a homozygous or heterozygous gene modification. With respect to the sample, it should be assumed that the assay material that contains the mutation gene to be analyzed is at least essentially not contaminated with wild-type genes. It can be thus envisaged, in the context of the method according to the present invention, that the melting curve with the highest melting point and/or the highest melting range is assigned to a homozygous gene modification for the case when the melting curve has a single melting point or melting range. The procedure can moreover be adopted, in the context of the method according to the present invention, such that the melting curve with the highest melting point or the highest melting range is assigned to a heterozygous gene modification for the case when the melting curve has two melting points or melting ranges that are different from one another.

For detecting homozygous or heterozygous gene modifications in a sample, which also contains the wild-type gene, the procedure can be, for example, that a first PCR assay of the sample without blocking agent and a second parallel PCR assay with blocking agent, optionally with another reference assay based on the wild-type gene, are carried out and analyzed. By comparing the formation of the melting points or ranges in particular with respect to the corresponding signal maxima of the wild-type gene or wild-type allele in the samples with or without blocking agent, an analysis for the presence of a homozygously or heterozygously formed mutation can be carried out.

Owing to the specific combination of all measures according to the present invention, it is possible in the context of the present invention that there is an at least 10-fold, in particular at least 50-fold, for example, at least 100-fold, for example, at least 500-fold, for example, at least 1000-fold intensification or amplification of detection with respect to the gene segment, in particular DNA segment, having the gene modification, of the mutation gene or of the associated (fluorescence) signal. In the context of the present invention, it is possible that there is an at least 10-fold, in particular at least 50-fold, for example, at least 100-fold, for example, at least 500-fold, for example, at least 1000-fold intensification and/or amplification of the measured signal associated with the gene segment, in particular DNA segment, having the gene modification, of the mutation gene.

As a result, it was possible, in the context of the present invention, based on the combination of the aforementioned measures, to provide an extremely sensitive detection of mutation. In the context of the present invention, a mutation can be analyzed or detected, even if only very small amounts of mutated DNA are present in the sample.

The method according to the present invention is equally suitable for carrying out monitoring based on the bodily material on which the sample is based, and in particular in, for example, peripheral blood, which makes it possible for the disease course to be monitored easily at the molecular level. Based on the method according to the present invention, optionally in combination with other purification techniques, in particular for specific purification or isolation of the DNA to be investigated from the sample, and which are familiar to a person skilled in the art, in the context of the present invention it is possible to detect circulating tumor cells in whole blood.

The method according to the present invention is therefore suitable for obtaining information for the diagnosis of oncosis or cancer or for determining the risk of falling ill with an oncosis or cancer, or for prognosis of the course of an oncosis or cancer or for prognosis of individual drug effects in the treatment of an oncosis and/or cancer. As a non-limiting example, a patient or test subject can thus be assigned an increased risk of falling ill with a bronchial carcinoma if they have one or more of the aforementioned mutations which can be detected on the basis of the method according to the present invention. Equally, a disease prognosis or a disease course can be recorded or analyzed, wherein respective samples are taken from the patient or test subject over a specified period and can be analyzed on the basis of the method according to the present invention and detection of the corresponding mutations indicates the presence of tumor cells in the sample.

It is equally possible, in the context of the present invention, based on concrete analysis of the underlying mutation, to optimize the therapeutic approach in particular with respect to the specific medication. Based on the mutations found, the drugs specific to each case or having the optimum action in this respect are thus used, which leads to further individualization and specialization of the medication or therapy, accompanied by higher therapeutic efficacy. If the T790M mutation is present, optionally in combination with the L858R mutation, application or administration of the second-generation inhibitors described above may thus be indicated, whereas if the L858R mutation is present, administration of the first-generation inhibitors described above may be indicated.

As already mentioned, the method according to the present invention can be used for mutation analysis in the case of bronchial carcinomas and in particular in the case of non-small-cell lung cancer or NSCLC with the respective involvement of the EGF receptor.

In an embodiment, the present invention provides a method of detecting a gene modification, in particular mutation, in a gene coding for the EGF receptor, wherein the EGF receptor is linked in particular to an oncosis or cancer, in particular a lung cancer, such as non-small-cell lung cancer (NSCLC), in particular wherein the gene having the gene modification (mutation gene) is present together with other genes coding for the protein, but not having a gene modification (wild-type genes). The method according to this aspect of the present invention is also characterized in that it is carried out by means of the asymmetric polymerase chain reaction in combination with the use of at least one detectable mutation-specific hybridization probe (sensor probe) on the one hand and at least one wild-type specific blocking agent inhibiting the binding of the sensor probe to the wild-type gene, in particular so that there is a selective intensification and/or amplification of the detection with respect to a gene segment, in particular DNA segment, of the mutation gene having the gene modification.

The methods of the present invention, according to the above aspects, can be carried out as such on the basis of methods familiar to a person skilled in the art employing the appropriate apparatus and measuring devices. For example, the polymerase chain reaction and the recording and analysis of the corresponding melting curves can be carried out using a LightCycler®-480 instrument from the company F. Hoffmann-La Roche Ltd.

In an embodiment, the present invention provides a composition in particular for use in the context of an asymmetric polymerase chain reaction, for example, for detecting at least one gene modification, in particular mutation, in a gene, for example, in a gene coding for a protein connected with an oncosis and/or cancer, in particular wherein the gene having the gene modification (mutation gene) is present together with other genes coding for the protein, but not having a gene modification (wild-type genes), wherein the composition in combination contains:

(a) a detectable mutation-specific hybridization probe (sensor probe);
(b) a first primer, which is bound at least substantially specifically to the single-stranded DNA of the mutation gene (probe strand), with which the sensor probe is capable of interacting;
(c) a second primer, which is capable of interacting at least substantially specifically with the single-stranded DNA of the mutation gene complementary to the probe strand (complementary strand);
(d) a wild-type specific blocking agent inhibiting the binding of the sensor probe to the wild-type gene;

wherein the content of the first primer (b) in the composition is greater than the content of the second primer (c).

Regarding the composition according to the present invention, this can contain (a) the hybridization probe or sensor probe in an amount from 0.01 to 5 pmol/µl, in particular 0.05 to 3 pmol/µl, for example, 0.1 to 1 pmol/µl, relative to the composition.

The composition according to the present invention can moreover contain (b) the first primer in a concentration from 0.05 to 10 pmol/µl, in particular 0.1 to 5 pmol/µl, for example, 0.2 to 2 pmol/µl, relative to the composition.

The composition according to the present invention can furthermore contain (c) the second primer in a concentration from 0.005 to 5 pmol/µl, in particular 0.01 to 2 pmol/µl, for example, 0.03 to 0.5 pmol/µl, relative to the composition.

The composition according to the present invention should contain (a) the first primer and (b) the second primer in a quantitative ratio of the (a) first primer to (b) the second primer ((a): (b)), relative to the composition, in the range from 1000:1 to 1.05:1, in particular 100:1 to 1.5:1, for example, 10:1 to 2:1.

The composition can moreover contain (d) the blocking agent in a concentration from 0.005 to 4 pmol/µl, in particular 0.01 to 1 pmol/µl, for example, 0.015 to 0.1 pmol/µl, relative to the total volume of the composition.

Moreover, the composition according to the present invention can in particular contain (e) an anchor probe, in particular as defined above, in particular in an amount from 0.01 to 5 pmol/µl, in particular 0.05 to 3 pmol/µl, for example, 0.1 to 1 pmol/µl, relative to the composition.

The composition is in particular an aqueous solution or dispersion. In this connection, the composition can in particular contain PCR-pure water. The composition can moreover contain so-called 480-probes-master.

The present composition can be prepared or batched ready for use and can be cooled or frozen for storage.

In the context of the present invention it is equally also possible for the composition to be in the form of components that are at least partially spatially separate from one another, in particular as a kit-of-parts, wherein the components (a) to (d) and optionally (e) can be at least partially separate from one another. In this respect, the components or ingredients can be brought together, for example, immediately before carrying out a test, to obtain a composition that is ready for use.

In an embodiment, the present invention provides a use of the composition according to the present invention, as defined above, for detecting at least one gene modification, in particular mutation, in a gene, for example, in a gene coding for a protein connected with an oncosis and/or cancer, in particular wherein the gene having the gene modification (mutation gene) is present together with other genes coding for the protein, but not having a gene modification (wild-type genes), in particular in the context of an asymmetric polymerase chain reaction.

FIG. 1 shows the structure of the EGF receptor. The growth receptor consists of an extracellular domain and an intracellular domain and a transmembrane domain. The ligand EGF is bound in the ligand binding site of the receptor in the extracellular region. In the intracellular region, there are the phosphorylation site and the deletions in exon 19 and the point mutations L858R and T790M.

Figure 2:
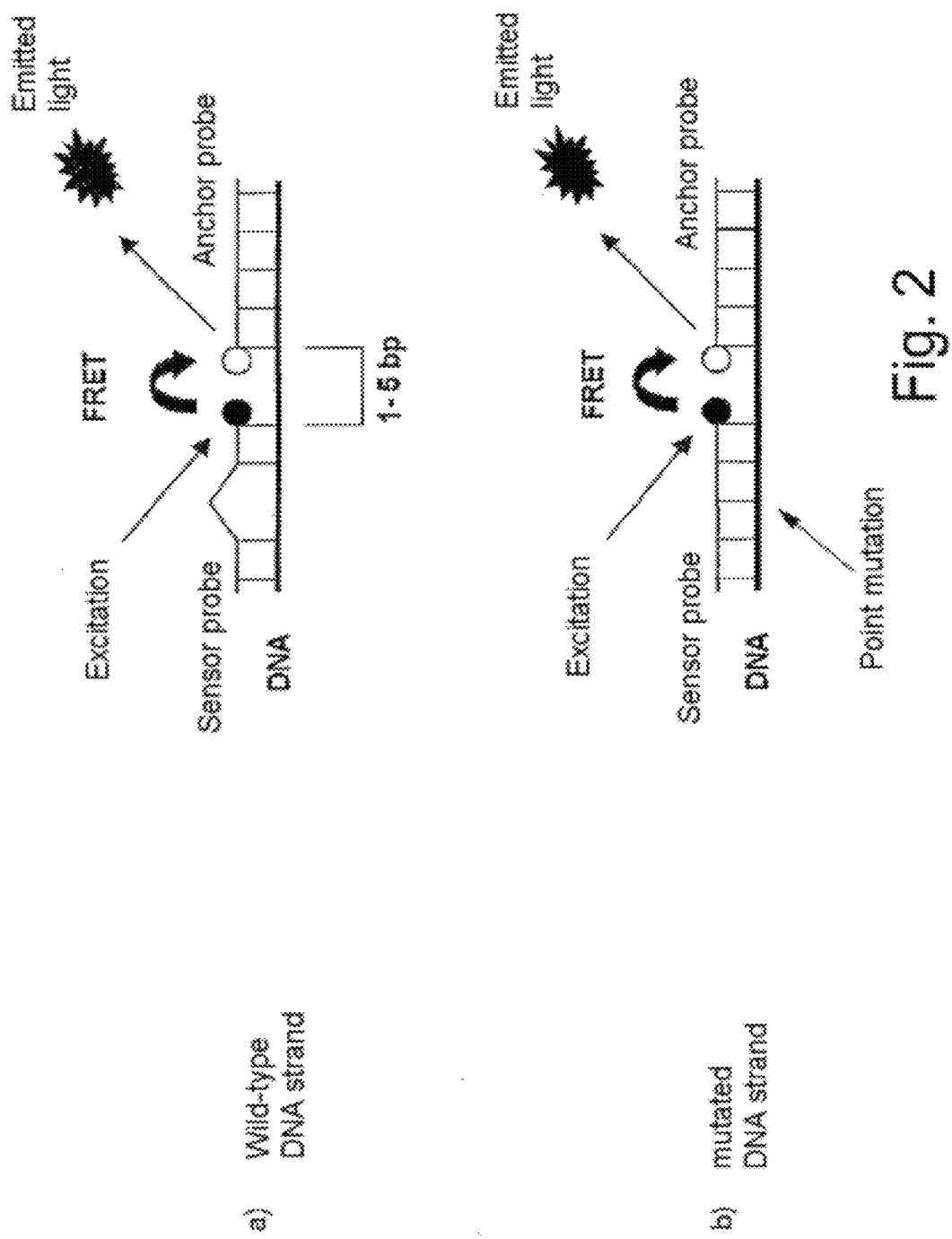
FIG. 2 shows the detection principle using hybridization probes based on mutation-specific sensor probes on the one hand and anchor probes on the other hand and the formation of a FRET signal.

Furthermore, FIG. 2 clarifies the detection principle using hybridization probes. In this connection, FIG. 2 a) shows the binding of the two hybridization probes to a single-stranded DNA with wild-type sequence. As the sensor probe binds specifically to the mutated strand, it can in this case only hybridize non-specifically to the wild-type strand. The fluorescent dye of the sensor probe is excited by light, the energy is transferred by FRET (fluorescence resonance energy transfer) to the fluorescent dye of the anchor probe, and the emitted light can be measured. In the context of the present invention, however, it is also possible, as mentioned above, for the sensor probe on the one hand and the anchor probe on the other hand each to be selected or labeled in such a way that—as it were conversely—energy transfer can take place from the anchor probe to the sensor probe. In this case there is therefore excitation of the fluorescent dye of the anchor probe and energy transfer by FRET to the sensor probe. For the energy transfer to take place, the base distance between the probes should not be more than 5 bp. FIG. 2 b) shows the binding of the respective hybridization probes—namely sensor probe on the one hand and anchor probe on the other hand—to a single-stranded DNA with mutation sequence or the gene modification to be detected. In this case, the sensor probe binds specifically in the mutation region. Through excitation of the fluorescent dye of the sensor probe and transfer of energy by FRET to the dye of the anchor probe, a signal is also emitted, which can be measured.

Figure 3:
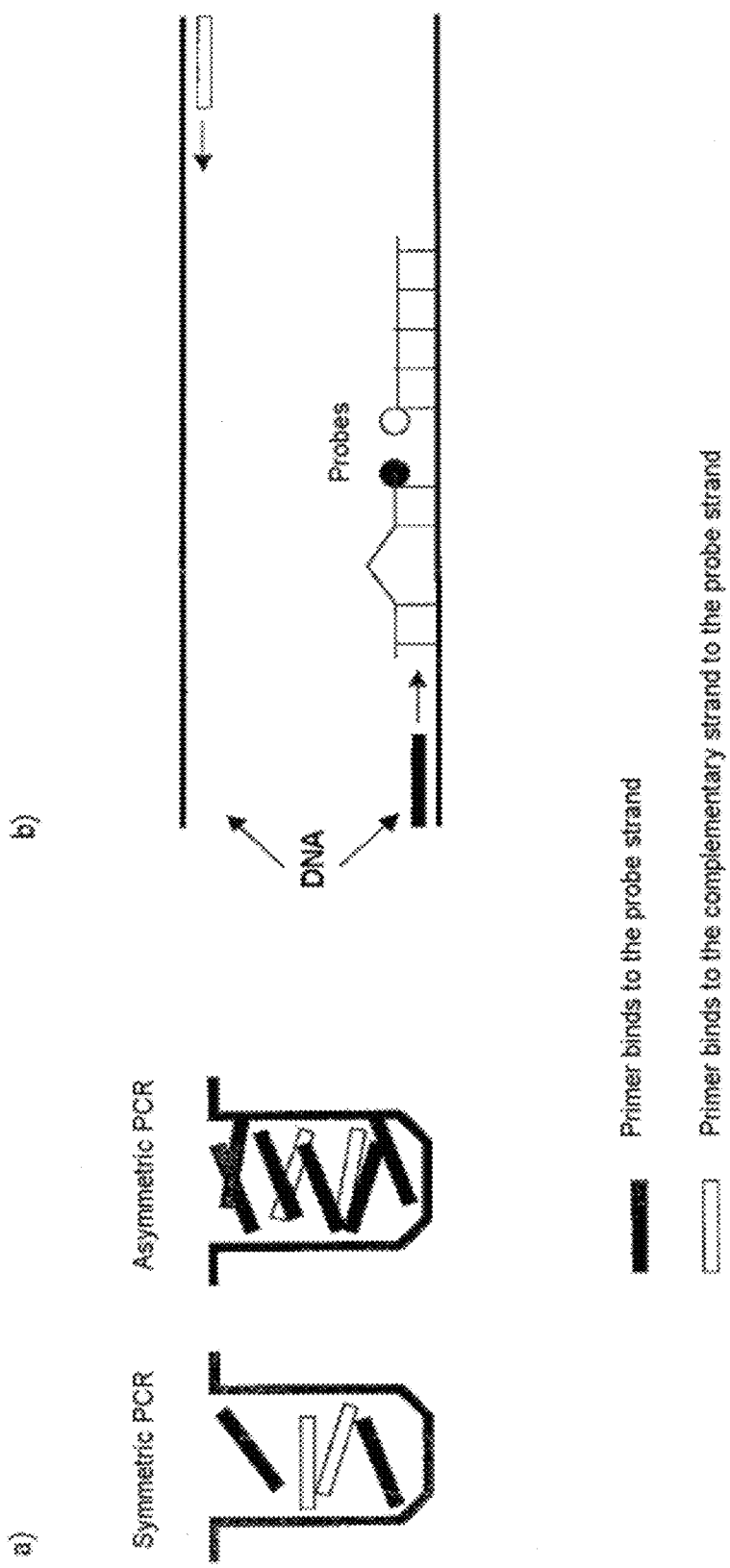
FIG. 3 shows the principle of asymmetric PCR.

Furthermore, FIG. 3 clarifies the principle of the asymmetric PCR used according to the present invention. In this connection, FIG. 3 a) shows that—in contrast to symmetric PCR—the primer ratio in asymmetric PCR is not identical. The concentration of the primer that binds to the probe strand is increased (shown in black). FIG. 3 b) shows an overview according to which the black-labeled primer binds to the probe strand, whereas the primer shown in white binds to the complementary single-strand of DNA.

Figure 4:
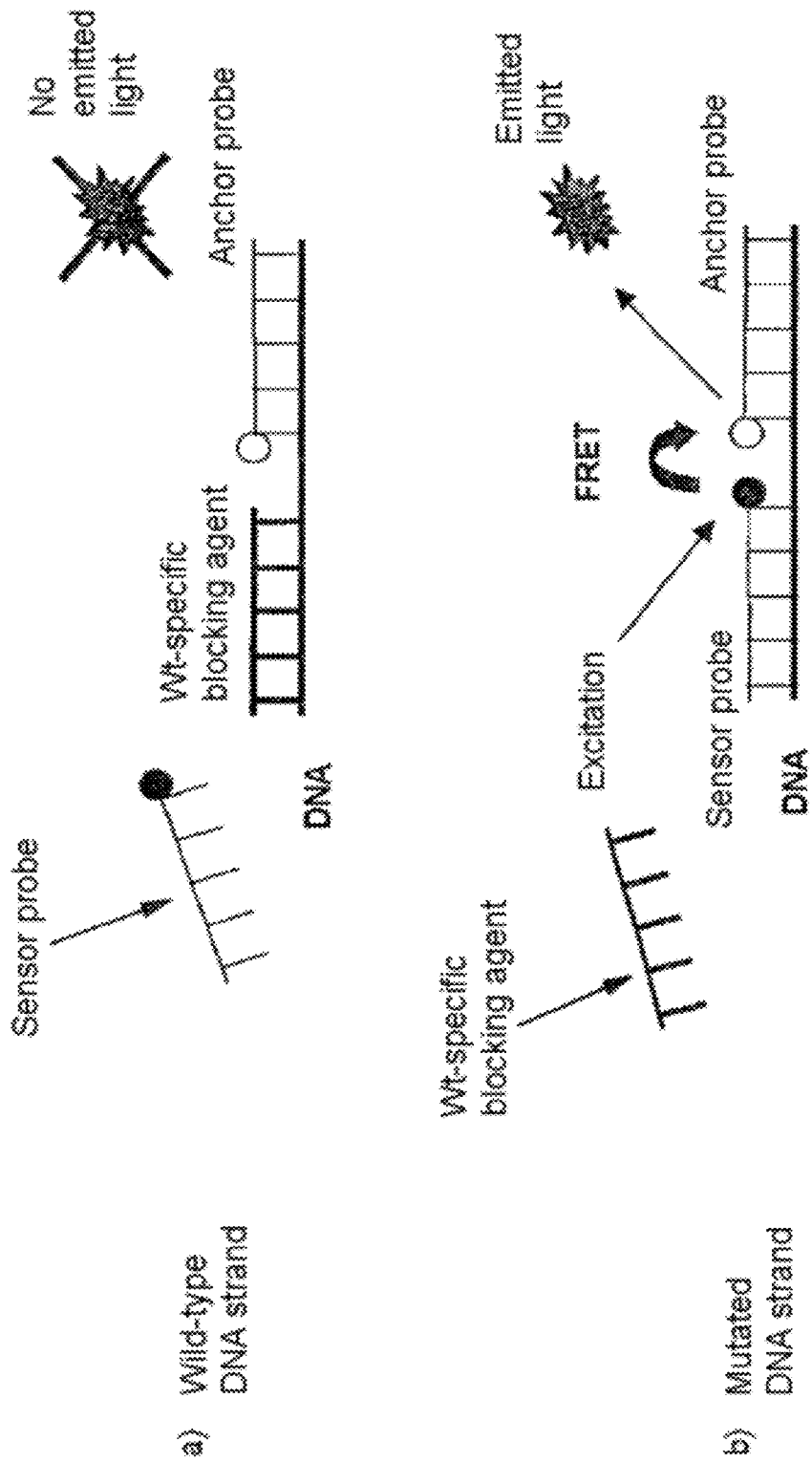
FIG. 4 shows the principle of inhibition of the wild type by the blocking agent used according to the present invention.

FIG. 4 illustrates the principle of inhibition of the wild-type DNA single-strand by the blocking agent used according to the present invention. FIG. 4 a) shows the binding of the blocking agent specific to the wild type (wt) to the wild-type DNA single-strand. The sensor probe can thus no longer hybridize at this site. The wt-DNA is moreover no longer amplified and also does not emit a signal in the absence of FRET. FIG. 4 b) shows the situation according to which the blocking agent cannot bind to the mutated single-strand of DNA, but the sensor probe. The mutated DNA is amplified and emits a signal, in particular in the form of light, which can be measured.

Figure 5:
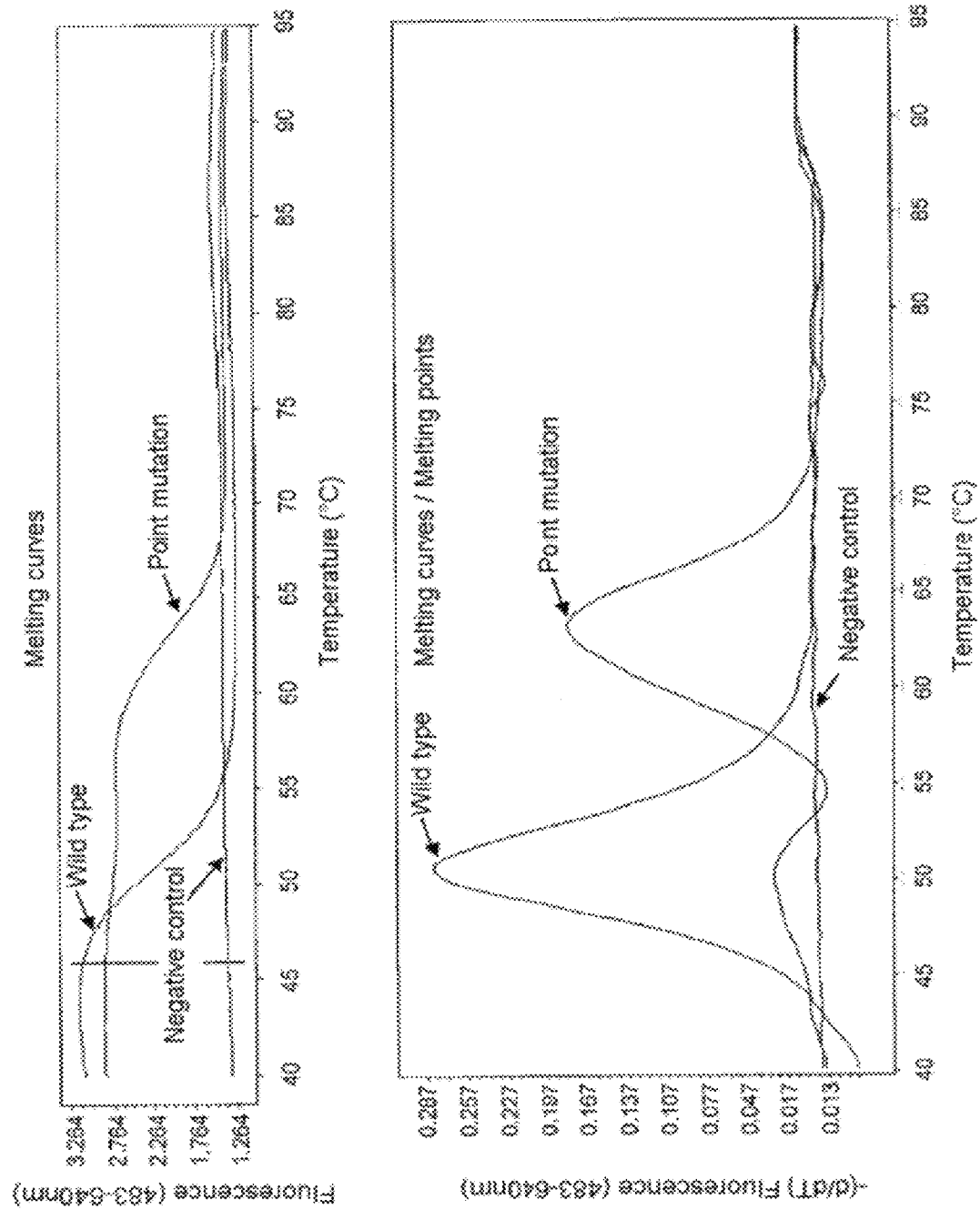
FIG. 5 shows a representation of specific melting curves using a LightCycler® 480 apparatus.

FIG. 5 shows a representation of the specific melting curves. After the actual PCR, a melting curve analysis is carried out. The top part of the figure shows the decrease in fluorescence with increasing melting temperature or sample temperature. The bottom part of the diagram shows the turning point of the measured fluorescence decrease as a curve. The curve with the maximum exclusively on the left (at low temperatures) shows a wild-type sample, the flat curve shows a negative control and the curve with the maximum on the right (at high temperatures) shows a heterozygous sample. A heterozygous sample is characterized in that it has a wild-type and a mutated allele. For this reason, heterozygous samples also display a so-called "double peak", i.e., two melting points or two melting point ranges.

Figure 6:
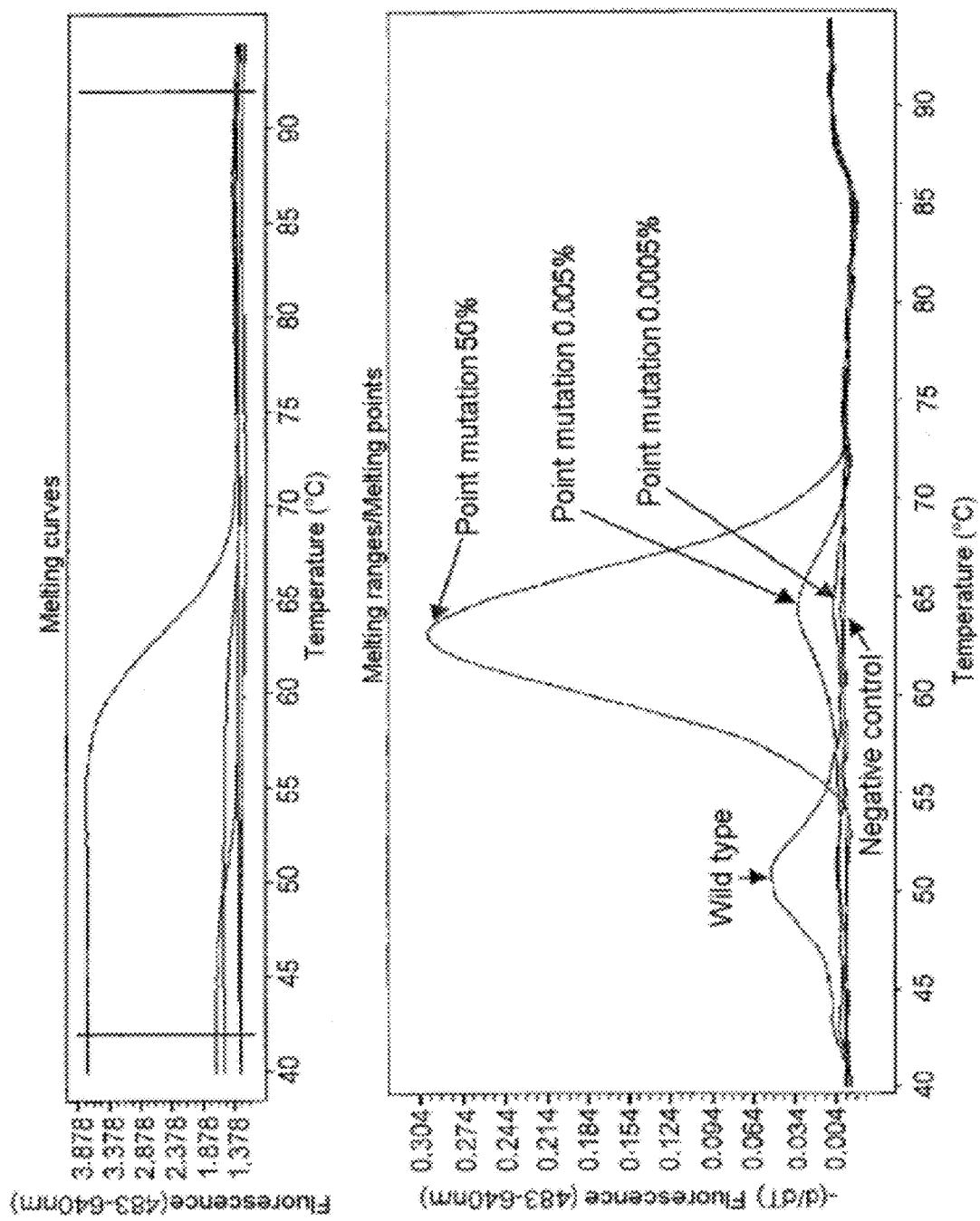
FIG. 6 shows a representation of specific melting curves of the L858R mutation with additional use of a blocking agent.

FIG. 6 shows the representation of the specific melting curves for the L858R mutation. The decrease in fluorescence is measured during the melting curve analysis. The signal of the wild type (maximum on the left) is inhibited almost completely in samples that comprise wild-type DNA exclusively. Samples with the point mutation in question, regardless of whether they are homozygous or heterozygous, can be detected by a peak or a maximum with higher melting temperature (maxima on the right). Samples that contain a minimal content of mutated DNA also have a curve at the specific melting temperature of the mutants. In this case, a proportion of just 0.0005% of L858R-mutated cells can be detected in a wild-type mixture, relative to the total cell content.

Figure 7:
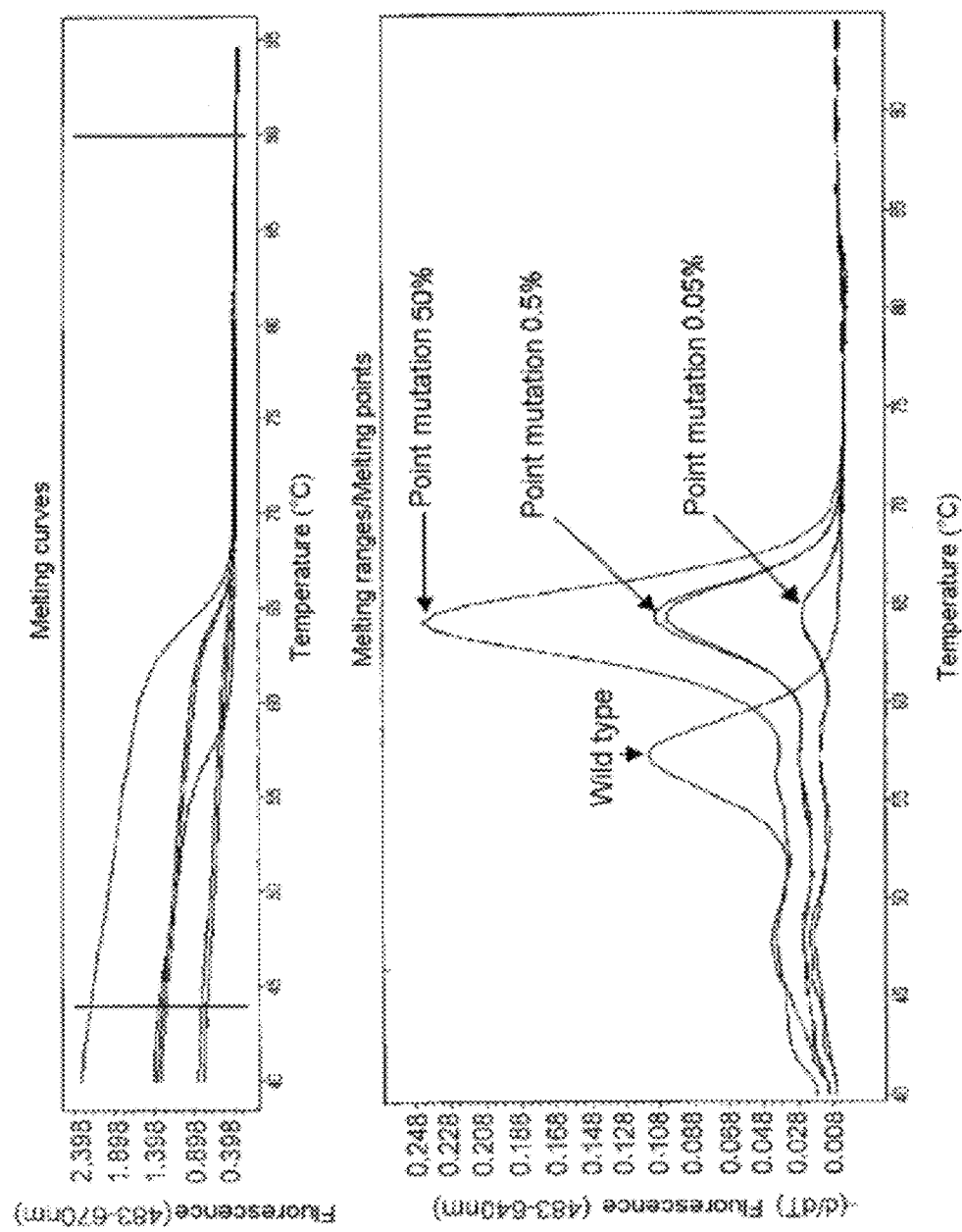
FIG. 7 shows a representation of specific melting curves of the T790M mutation with addition of a blocking agent.

Finally, FIG. 7 shows a representation of the specific melting curves of the T790M mutation. The decrease in fluorescence is measured during the melting curve analysis. The signal of the wild type (maximum on the left) is almost inhibited in samples that comprise wild-type DNA exclusively. Samples with the point mutation in question, regardless of whether they are homozygous or heterozygous, can be detected by a peak or a maximum with higher melting temperature (maxima on the right). Samples that only contain a minimum content of mutated DNA also have a curve at the specific melting temperature of the mutants. With respect to the T790M mutation, a proportion of just 0.05% of T790M-mutated cells, relative to the total content of cells in the sample, can be detected in a wild-type mixture.

The present invention is illustrated further, non-exhaustively, below:

In connection with the present invention, it could be shown that the activation of the EGF receptor (EGFR) can be inhibited by EGFR inhibitors. Over 80% of the mutations of the EGF receptor in NSCLC patients are based on various deletions in exon 19, and on a point mutation in exon 2, namely L858R (exchange of the amino acid leucine L at position 858 for arginine R, cf. FIG. 1). Patients with a lung tumor, who have one of these changes, are therefore especially suitable for therapy with EGFR inhibitors.

Although the therapy is in general well-tolerated and is very specifically effective, after a certain time most patients develop a so-called secondary mutation, which can occur in addition to the mutation already present and leads to resistance to erlotinib and gefitinib. In roughly 50 to 65% of these cases the mutation T790M is found (exchange of the amino acid threonine T for methionine M at position 790, cf. FIG. 1). For these patients, drugs are available whose mechanism of action differs from those of the first generation (erlotinib, gefitinib). These so-called second-generation inhibitors bind irreversibly to the receptor and not reversibly, e.g. Tarceva® or Iressa™. NSCLC patients, who on account of the T790M mutation no longer respond to the first-generation drugs, can therefore be treated further with a second-generation EGFR inhibitor (e.g. BIBW2992/Tovok from Boehringer Ingelheim). Clinical studies have shown that these inhibitors are also highly specific and effective, so that the growth and survival of the tumor cells can be slowed or prevented.

In the sense of individualized medicine, i.e., being able to offer each individual patient with NSCLC the therapy that is most suitable for him, it is necessary and sensible to test the tumor tissue for EGFR status. Patients who have an activating mutation in the EGF receptor can therefore be offered treatment with the corresponding EGFR inhibitors.

In order to achieve a high degree of sensitivity, various optimization steps are carried out in the context of the present invention, and will be illustrated below for the example of the point mutation L858R.

At the start of planning or execution of mutation detection, first specific primers and hybridization probes are generated or provided. Said primers and hybridization probes can be obtained, for example, from the company TIB MOLBIOL GmbH, Berlin.

The specific primers preferentially amplify the segment of the DNA in which the mutation to be detected is localized. In addition, in the PCR reaction according to an embodiment, two hybridization probes that are different from one another (sensor probe on the one hand and anchor probe on the other hand) are used. These comprise, as do the primers, several nucleotides which hybridize within the PCR product that forms. The two probes bind in close spatial proximity. On the ends opposite one another, the probes are each labeled with a fluorescent dye and can interact with one another by FRET (fluorescence resonance energy transfer) (cf. FIG. 2). The probes bind both in and on the wild-type sequence (wild-type DNA single-strand or wild-type DNA strand) and on the mutation sequence (mutated DNA single-strand or mutated DNA strand), wherein one of the probes (anchor probe) binds in the unaltered sequence region and the other probe (sensor probe) binds in the region of the presumed (point) mutation.

If a point mutation is present at the binding site and if the sensor probe was synthesized to match the mutated sequence, this probe binds specifically. If no point mutation is present, the sensor probe binds correspondingly non-specifically. In both cases, during or after energetic excitation with electromagnetic radiation of a corresponding wavelength, such as can be produced by the xenon lamp of the LightCycler®, the sensor probe transfers its energy by FRET to the anchor probe. This is also excited as a result and emits a fluorescence signal, which can be detected by the equipment. The measurement can be carried out at the end of the annealing phase of each PCR cycle, the phase in which the primers and probes bind to the DNA strand.

The actual PCR is followed by a melting curve analysis. In this, the reaction mixtures are heated slowly, for example to 95° C. At the point when 50% of the sensor probes have detached from the resultant PCR products, there is an abrupt drop in fluorescence. If the probe binds specifically to the mutated strand, the dehybridization or detachment of the sensor probe takes place at a higher temperature compared to binding on wild-type sequences. In addition to the decrease in the fluorescence signal with increasing temperature, in particular when using the LightCycler® 480, the first mathematical derivative of the cleavage curve is calculated, so that the turning point of the measured fluorescence decrease is shown as a curve. The highest point or maximum of the curve, based on the first derivative, corresponds to the specific melting temperature. This representation serves for better visual evaluation. Heterozygous samples, i.e., cells possessing both a wild-type and a mutated allele, therefore show two different melting profiles, which can correspondingly be seen as a "double peak" or double maximum (formation of two different maxima) (cf. FIG. 3).

After any optimization of the amount of DNA used, of the annealing temperature, of primer compatibility and/or concentration and of the probe concentration, detection of the L858R mutation under conditions of the prior art in the context of a usual and non-asymmetric PCR, just as in the case of sequencing, shows a sensitivity of only 20 to 25%.

In order to raise the limit of detection, in the context of the present invention, a so-called asymmetric PCR is applied or carried out appropriately. In contrast to the symmetric PCR, the ratio of the two primers to one another is not equal. The concentration of the primer that binds to that DNA strand to which the probes also hybridize (probe strand), is increased in the PCR assay. This strand is therefore multiplied preferentially and the probes used therefore have a higher probability of binding to this strand (cf. FIG. 3). In this way the sensitivity of mutation detection can also be increased.

For a further increase in sensitivity, it is further envisaged according to the present invention to reduce or inhibit the amplification of the wild-type DNA strand and/or the binding of the sensor probe to the wild-type DNA strand, so that only or primarily the mutated DNA strand is replicated and the probes used can therefore as it were bind without competition to the mutated DNA. By means of this technique according to the present invention, as a complete surprise, even extremely small amounts of mutated material can be detected. This specific inhibition of the wild type can be performed e.g., with a blocking agent, in particular in the form of a so-called locked nucleic acid (LNA™ from the company Exiqon), which is also called a "Clamp" (cf. FIG. 4). These "clamps" are modified biochemically so that they have a very high binding strength against the wild-type strand and only melt at very high temperatures.

The decrease in fluorescence is measured during the melting curve analysis. If a mutation is to be detected in the sample, the corresponding curve is visible; if no mutated material is present, no or a minimal wild-type curve can be seen, because owing to the absence of amplification and probe binding of the wild type, no signal can be measured (cf. FIG. 6 and FIG. 7).

So as to be able to confirm that the PCR reaction has been carried out successfully and to be able to detect heterozygotes, a comparative assay without blocking agent should also be run concurrently or should be carried out. At least the wild type should be visible in this reaction.

The combination of the aforementioned measures according to the present invention makes detection of mutations possible with extremely high sensitivity. In the aforementioned example of detection of the L858R mutation, a sensitivity of 0.0005% of mutated DNA in a wild-type mixture can be achieved. Therefore extremely small proportions of mutated DNA for example of a tumor tissue in a sample can be detected. The method according to the present invention is also suitable for monitoring in the peripheral blood or other body fluids. For many patients with solid tumors, e.g. NSCLC patients, generally tumor material is only obtained once, e.g., on initial diagnosis or during an operation. Therefore monitoring or observation of the course of the disease at the molecular level is not generally possible. With the highly sensitive detection method according to the present invention, which can also be carried out in combination with sensitive purification techniques, even circulating tumor cells in a whole blood sample can be detected. It has, for example been described that patients with NSCLC have about 100 to 200 circulating tumor cells per 1 ml of blood. Assuming about 10,000 nucleated cells per µl, this means a content of about 0.001% of tumor cells. With the real-time PCR method according to the present invention, which can also comprise a sensitive method of purification of the tumor cells, this detection and therefore monitoring are possible for patients before or during therapy. The present invention therefore represents an important step in the direction of individualized and thus highly specific therapy.

Further embodiments, modifications and variations of the present invention can be recognized and can be carried out readily by a person skilled in the art on reading the description, while remaining within the scope of the present invention.

The following example serves solely for illustration of the present invention, but the present invention is not limited to this.

EXAMPLE

Detection of EGFR-T790M Mutation

Detection of the mutation T790M in genomic DNA by melting curve analysis on the LightCycler® 480:

Additional Reference Documents
 Data sheet "LightCycler 480 Probes Master" from F. Hoffmann-La Roche Ltd.;
 Data sheet "PureLink Genomic DNA Mini Kit" from Invitrogen Corp.

Materials
 LightCycler® 480 Probes Master Kit from F. Hoffmann-La Roche Ltd. (order No. 04887301001);
 Primers and probes from TIB MOLBIOL GmbH, Berlin: Primers: EGFR F (product No. 1030632) and EGFR A (product No. 1030635); Probes: Anchor_790 (product No. 1030640) and Sensor [T] (product No. 1030639) and 790 LNA wt (product No. 1084404);
 Genomic DNA, e.g. from peripheral blood (citrate); (20-90 µg/ml initial concentration); isolated with "PureLink Genomic DNA Mini Kit" from Invitrogen Corp. (order No. K1820-01);
 Control DNA: e.g. A431 (EGFR Wild Type) and H1975 (EGFR L858R mutant);
 96-well plates from F. Hoffmann-La Roche Ltd., white (LightCycler 480-Multiwell-Plate 96, order No. 04729692001)

Equipment
 Centrifuge with insert for 96-well plates (e.g. Multifuge 3SR+ from Thermo Fisher Scientific Inc.);
 LightCyclery® 480 from F. Hoffmann-La Roche Ltd. with 96-well block.

Description of Procedure
 Thawing of the necessary kit components, primers and probes on ice (thaw probes in the dark)
Pipetting of the Primer/Probe Mix onto Ice

| EGFR F: | 0.4 µl (8 pmol) | 20 pmol/µl |
|---|---|---|
| +EGFR A: | 0.06 µl (1.2 pmol) | 20 pmol/µl |
| +Anchor_790: | 0.15 µl (3 pmol) | 20 pmol/µl |
| +Sensor [T]: | 0.15 µl (3 pmol) | 20 pmol/µl |
| +790 LNA wt: | 0.275 µl (0.55 pmol) | 2 pmol/µl |
| +PCR-pure water: | 0.965 µl | |

Total volume: 2 µl

Pipetting of the Master Mix
 Primer/probe mix according to above details: 2 µl
 + 480-Probes Master: 10 µl
 + PCR-pure water: 7.5 µl
 Total volume: 19.5 µl
 Pipette 19.5 µl Master Mix and 0.5 µl DNA into a white 96-well plate. Run concurrently a water control without DNA, a negative control (wild type, e.g. A431) and a positive control (mutant, e.g. H1975). In addition, carry out an assay without LNA probe (corresponding proportion of water in the primer/probe mix).
 Seal the plate with film, and centrifuge: 1500 g, 2 min at RT
 Put the plate in LightCycler® 480 and start program:

| Filter combinations: | Melting factor: | Quant factor: | Max. Integration Time: |
|---|---|---|---|
| 483-640 | 1.2 | 5 | 2 seconds |

| Procedure: | Temperature | Time | Cycles |
|---|---|---|---|
| 1. Preincubation: | 95° C. | 00:10:00 | 1 |
| 2. Amplification: | 95° C. | 00:00:10 | 40 |
| | 56° C. | 00:00:10 | |
| | 72° C. | 00:00:10 | |
| 3. Melting curve: | 95° C. | 00:01:00 | 1 |
| | 40° C. | 00:02:00 | |
| | 95° C. | continuous | |
| 4. Cooling | 4° C. | continuous | |

Expected result of the melting curve analysis:

| Result: | Melting-Curve Temperatures |
|---|---|
| Probes bind specifically to mutant | |
| homozygous mutant: | a melting curve between 55 and 70° C. |
| homozygous wild type: | a melting curve between 45 and 60° C. |
| heterozygote: | two melting curves; see above |

Information and notes: The prepared PCR mix is stable for at least 24 hours at RT in the dark.
 Abbreviation: RT=room temperature
 The present invention is not limited to embodiments described herein; reference should be had to the appended claims.

What is claimed is:

1. A method of detecting at least one gene modification such as a mutation in a gene, the method comprising:

carrying out an asymmetric polymerase chain reaction (PCR) using a PCR reaction mixture comprising at least one detectable mutation-specific hybridization probe (sensor probe) and at least one wild-type specific blocking agent which inhibits a binding of the at least one detectable mutation-specific hybridization probe (sensor probe) to a wild-type gene so as to provide at least one of a selective intensification and an amplification of a detection of a gene segment of a mutation gene having a gene modification, wherein, the at least one wild-type blocking agent is selected so that the at least one wild-type blocking agent has a higher specificity for an area of a DNA single strand of the wild-type gene, which corresponds to the gene section of the mutation gene having the mutation, compared to the mutation gene.

2. The method as recited in claim 1, wherein the gene segment is a DNA segment.

3. The method as recited in claim 1, wherein the mutation in the gene is a gene coding for a protein associated with at least one of a tumor and a cancer.

4. The method as recited in claim 3, wherein the mutation gene is present together with wild-type genes coding for the protein, wherein the wild-type genes do not comprise the gene modification.

5. The method as recited in claim 3, wherein the at least one of an oncosis and a cancer is a lung cancer such as at least one of a non-small-cell lung cancer (NSCLC), a small-cell lung cancer (SCLC), and a non-small-cell lung cancer (NSCLC).

6. The method as recited in claim 3, wherein the protein is at least one of a human protein, a protein which at least one of regulates and induces at least one of a cell growth and a cellular proliferation, a protein which is a transmembrane receptor for growth factors such as a protein with an intrinsic tyrosine kinase activity, and a protein with an epidermal growth factor receptor (EGF receptor).

7. The method as recited in claim 1, wherein the gene modification at least one of:

brings about a deletion in exon 19 of a EGF receptor, is associated with the deletion in exon 19 of the EGF receptor, brings about an exchange of at least one amino acid in at least one of exon 20 and exon 21 of the EGF receptor, is associated with the exchange of at least one amino acid in at least one of exon 20 and exon 21 of the EGF receptor, brings about an exchange of serine at position 768 of the EGF receptor such as via isoleucine (S768I), is associated with the exchange of serine at position 768 of the EGF receptor such as via isoleucine (S768I), brings about an exchange of threonine at position 790 of the EGF receptor such as via methionine (T790M), is associated with the exchange of threonine at position 790 of the EGF receptor such as via methionine (T790M), brings about an exchange of leucine at position 858 of the EGF receptor such as via arginine (L858R), and is associated with the exchange of leucine at position 858 of the EGF receptor such as via arginine (L858R).

8. The method as recited in claim 1, further comprising at least one of:

carrying out the asymmetric polymerase chain reaction (PCR) in the presence of primers such as in the form of oligonucleotides, amplifying the gene segment of the mutation gene corresponding to a deletion in exon 19 of a EGF receptor, amplifying the gene segment of the mutation gene corresponding to an exchange of serine at position 768 of the EGF receptor such as via isoleucine (S768I), amplifying the gene segment of the mutation gene corresponding to an exchange of threonine at position 790 of the EGF receptor such as via methionine (T790M), amplifying the gene segment of the mutation gene corresponding to an exchange of leucine at position 858 of the EGF receptor such as via arginine (L858R), amplifying the gene segment of a wildtype gene corresponding to the gene segment of the mutation gene having the gene modification, binding a first primer at least substantially specifically to a single-stranded DNA of the mutation gene (probe strand) with which the at least one detectable mutation-specific hybridization probe (sensor probe) can interact, binding a second primer at least substantially specifically to a single-stranded DNA of the mutation gene complementary to the probe strand (complementary strand), and selecting the first primer and the second primer so that at least one of an amount and a concentration of the first primer, such as relative to a PCR assay, is greater than the at least one of an amount and a concentration of the second primer so as to at least one of increase and intensify an amplification of the probe strand vis-à-vis the complementary strand.

9. The method as recited in claim 1, wherein the at least one detectable mutation-specific hybridization probe (sensor probe) is selected so that the at least one detectable mutation-specific hybridization probe (sensor probe) at least one of:

has at least one of a higher specificity, a higher binding affinity and a higher selectivity with respect to a single-stranded DNA of the mutation gene (probe strand), such as in a region of the gene modification, vis-à-vis a corresponding single-stranded DNA of the wild-type gene, can emit at least one of a detectable signal and a measurable signal, such as a fluorescence signal, in the case of at least one of an interaction and a binding to at least one of a single-stranded DNA of the mutation gene (probe strand) and a corresponding single-stranded DNA of the wild-type gene, and can emit no, at least one of a reduced detectable signal and a reduced measurable signal, or a detectable signal or a measurable signal different from a bound state in the case of at least one of an induced detachment of the single-stranded DNA from the mutation gene (probe strand), such as a heat-induced detachment of the single-stranded DNA from the mutation gene (probe strand), and of a corresponding single-stranded DNA from the wild-type gene.

10. The method as recited in claim 9, wherein the region of the gene modification is a gene mutation.

11. The method as recited in claim 1, further comprising at least one of:

using in addition to the at least one detectable mutation-specific hybridization probe (sensor probe) at least one second hybridization probe (anchor probe) different from the at least one detectable mutation-specific hybridization probe (sensor probe), selecting the at least one detectable mutation-specific hybridization probe (sensor probe) and the at least one second hybridization probe (anchor probe), such as selecting a detectable substance of the at least one detectable mutation-specific hybridization probe (sensor probe) and a detectable substance of the at least one second hybridization probe (anchor probe), so that the at least one detectable mutation-specific hybridization probe (sensor probe) and the at least one second hybridization probe (anchor probe) can form a FRET pair, and selecting the at least one second hybridization probe (anchor probe) so that the at least one second hybridization probe (anchor probe) can bind to a same single-stranded DNA as the at least one detectable mutation-specific hybridization probe (sensor probe), such as binding the at least one second hybridization probe (anchor probe) at a distance of from 1 to 5 bp (base pairs) from the at least one detectable mutation-specific hybridization probe (sensor probe).

12. The method as recited in claim 1, wherein the wild-type specific blocking agent is selected to have at least one of a higher specificity, a higher binding affinity and a higher selectivity with respect to a single-stranded DNA of the wild-type gene, such as with respect to a region of the single-stranded DNA of the wild-type gene, which corresponds to the gene segment of the mutation gene having the gene modification, vis-à-vis a corresponding mutation gene.

13. The method as recited in claim 1, wherein the method further comprises at least one of:

recording a melting curve, carrying out a melting curve analysis, detecting at least one of a cleavage and a dehybridization, such as of the at least one detectable mutation-specific hybridization probe (sensor probe), from a single-stranded DNA of the at least one of the mutation gene and the wild-type gene, concluding a presence of a mutation from at least one of a melting point, melting points and melting point ranges of the melting curve, and determining a mutation type if the presence of a mutation is concluded.

14. The method as recited in claim 13, wherein the asymmetric polymerase chain reaction (PCR) is carried out first.

15. The method as recited in claim 13, wherein the detecting occurs photometrically, such as by measuring a fluorescence.

16. A composition for use in an asymmetric polymerase chain reaction (PCR), such as to detect at least one gene modification such as a mutation in a gene, the compostion comprising:

a detectable mutation-specific hybridization probe (sensor probe);

a first primer which binds at least substantially specifically to a single-stranded DNA of the mutation gene (probe strand), with which the detectable mutation-specific hybridization probe (sensor probe) can interact;

a second primer which can interact at least substantially specifically with a single-stranded DNA of the mutation gene complementary to the probe strand (complementary strand); and a wild-type specific blocking agent which inhibits a binding of the detectable mutation-specific hybridization probe (sensor probe) to a wild-type gene, wherein a content of the first primer in the composition is greater than a content of the second primer and the detection of the at least one gene modification such as a mutation in a gene comprises: providing the composition as a PCR reaction mixture; and carrying out an asymmetric polymerase chain reaction (PCR) using the PCR reaction mixture so as to provide at least one of a selective intensification and an amplification of a detection of a gene segment of a mutation gene having a gene modification, wherein, the wild-type blocking agent is selected so that the wild-type blocking agent has a higher specificity for an area of a DNA single strand of the wild-type gene, which corresponds to the gene section of the mutation gene having the mutation, compared to the mutation gene.

17. The composition as recited in claim 16, wherein the gene codes a protein associated with at least one of an oncosis and a cancer.

18. The composition as recited in claim 17, wherein the gene having the gene modification (mutation gene) is present together with wild-type genes coding for the protein, wherein the wild-type genes do not comprise the gene modification.

19. A method of using the composition as recited in claim 16 to detect at least one gene modification, such as a mutation, in a gene, the method comprising:

providing the composition as recited in claim 16; and detecting at least one gene modification with the composition.

20. The method using as recited in claim 19, wherein the detecting occurs by carrying out an asymmetric polymerase chain reaction (PCR).

21. The method using as recited in claim 19, wherein the gene codes a protein associated with at least one of an oncosis and a cancer.

22. The method using as recited in claim 21, wherein the gene having the gene modification (mutation gene) is present together with wild-type genes coding for the protein, wherein the wild-type genes do not comprise the gene modification.

23. The method as recited in claim 1, wherein the method is performed on a mixture of a mutated DNA with a wild-type DNA where a content of the mutated DNA is about 0.0025% based on a total DNA content.

24. The method as recited in claim 1, wherein the method of detecting at least one gene modification is performed with a sample having fewer than 500 tumor cells per ml/sample.

25. The method as recited in claim 1, wherein the method of detecting at least one gene modification is performed with a DNA sample having less than 0.01% of tumor cells, based on a total cell content of the sample.

26. The method as recited in claim 1, wherein the method of detecting at least one gene modification is performed with a starting material having less than 0.005% of mutated DNA, based on a total DNA in the sample or in the starting material.

\* \* \* \* \*

SEQUENCE LISTING

<160> NUMBER OF SEQ ID NOS: 11

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

```
Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
```

```
             785                 790                 795                 800
        Tyr Val Arg Glu His Lys Asp Asn Ile Gly Ser Gln Tyr Leu Leu Asn
                            805                 810                 815

Trp Cys Val Gln Ile Ala Lys Gly Met Asn Tyr Leu Glu Asp Arg Arg
                            820                 825                 830

Leu Val His Arg Asp Leu Ala Ala Arg Asn Val Leu Val Lys Thr Pro
                            835                 840                 845

Gln His Val Lys Ile Thr Asp Phe Gly Leu Ala Lys Leu Leu Gly Ala
                850                 855                 860

Glu Glu Lys Glu Tyr His Ala Glu Gly Gly Lys Val Pro Ile Lys Trp
        865                 870                 875                 880

Met Ala Leu Glu Ser Ile Leu His Arg Ile Tyr Thr His Gln Ser Asp
                            885                 890                 895

Val Trp Ser Tyr Gly Val Thr Val Trp Glu Leu Met Thr Phe Gly Ser
                        900                 905                 910

Lys Pro Tyr Asp Gly Ile Pro Ala Ser Glu Ile Ser Ser Ile Leu Glu
                        915                 920                 925

Lys Gly Glu Arg Leu Pro Gln Pro Pro Ile Cys Thr Ile Asp Val Tyr
                930                 935                 940

Met Ile Met Val Lys Cys Trp Met Ile Asp Ala Asp Ser Arg Pro Lys
        945                 950                 955                 960

Phe Arg Glu Leu Ile Ile Glu Phe Ser Lys Met Ala Arg Asp Pro Gln
                        965                 970                 975

Arg Tyr Leu Val Ile Gln Gly Asp Glu Arg Met His Leu Pro Ser Pro
                        980                 985                 990

Thr Asp Ser Asn Phe Tyr Arg Ala Leu Met Asp Glu Glu Asp Met Asp
                    995                 1000                1005

Asp Val Val Asp Ala Asp Glu Tyr Leu Ile Pro Gln Gln Gly Phe
                1010                1015                1020

Phe Ser Ser Pro Ser Thr Ser Arg Thr Pro Leu Leu Ser Ser Leu
                1025                1030                1035

Ser Ala Thr Ser Asn Asn Ser Thr Val Ala Cys Ile Asp Arg Asn
                1040                1045                1050

Gly Leu Gln Ser Cys Pro Ile Lys Glu Asp Ser Phe Leu Gln Arg
                1055                1060                1065

Tyr Ser Ser Asp Pro Thr Gly Ala Leu Thr Glu Asp Ser Ile Asp
                1070                1075                1080

Asp Thr Phe Leu Pro Val Pro Glu Tyr Ile Asn Gln Ser Val Pro
                1085                1090                1095

Lys Arg Pro Ala Gly Ser Val Gln Asn Pro Val Tyr His Asn Gln
                1100                1105                1110

Pro Leu Asn Pro Ala Pro Ser Arg Asp Pro His Tyr Gln Asp Pro
                1115                1120                1125

His Ser Thr Ala Val Gly Asn Pro Glu Tyr Leu Asn Thr Val Gln
                1130                1135                1140

Pro Thr Cys Val Asn Ser Thr Phe Asp Ser Pro Ala His Trp Ala
                1145                1150                1155

Gln Lys Gly Ser His Gln Ile Ser Leu Asp Asn Pro Asp Tyr Gln
                1160                1165                1170

Gln Asp Phe Phe Pro Lys Glu Ala Lys Pro Asn Gly Ile Phe Lys
                1175                1180                1185

Gly Ser Thr Ala Glu Asn Ala Glu Tyr Leu Arg Val Ala Pro Gln
                1190                1195                1200
```

```
Ser Ser  Glu Phe Ile Gly Ala
    1205         1210

<210> SEQ ID NO 2
<211> LENGTH: 26
<212> TYPE: DNA
<213> ORGANISM: Artificial Sequence
<220> FEATURE:
<223> OTHER INFORMATION: PCR-oligonucleotide specific for the
      corresponding gene of human epidermal growth factor receptor
      (EGFR)

<400> SEQUENCE: 2
gactccgact cctcctttat ccaatg                                          26

<210> SEQ ID NO 3
<211> LENGTH: 21
<212> TYPE: DNA
<213> ORGANISM: Artificial Sequence
<220> FEATURE:
<223> OTHER INFORMATION: PCR-oligonucleotide specific for the
      corresponding gene of human epidermal growth factor receptor
      (EGFR)

<400> SEQUENCE: 3
cacacaccag ttgagcaggt a                                               21

<210> SEQ ID NO 4
<211> LENGTH: 19
<212> TYPE: DNA
<213> ORGANISM: Artificial Sequence
<220> FEATURE:
<223> OTHER INFORMATION: PCR-oligonucleotide specific for the
      corresponding gene of human epidermal growth factor receptor
      (EGFR)

<400> SEQUENCE: 4
gctcagagcc tggcatgaa                                                  19

<210> SEQ ID NO 5
<211> LENGTH: 19
<212> TYPE: DNA
<213> ORGANISM: Artificial Sequence
<220> FEATURE:
<223> OTHER INFORMATION: PCR-oligonucleotide specific for the
      corresponding gene of human epidermal growth factor receptor
      (EGFR)

<400> SEQUENCE: 5
catcctcccc tgcatgtgt                                                  19

<210> SEQ ID NO 6
<211> LENGTH: 20
<212> TYPE: DNA
<213> ORGANISM: Artificial Sequence
<220> FEATURE:
<223> OTHER INFORMATION: real-time PCR probe specific for point mutation
      T790M of the EGFR gene (sensor probe)
<220> FEATURE:
<221> NAME/KEY: misc_binding
<222> LOCATION: (1)..(1)
<223> OTHER INFORMATION: FRET-component, preferably fluorescent dye

<400> SEQUENCE: 6
ggcatgagct gcatgatgag                                                 20

<210> SEQ ID NO 7
```

```
<211> LENGTH: 23
<212> TYPE: DNA
<213> ORGANISM: Artificial Sequence
<220> FEATURE:
<223> OTHER INFORMATION: real-time PCR probe specific for point mutation
      T790M of the EGFR gene (anchor probe)
<220> FEATURE:
<221> NAME/KEY: misc_binding
<222> LOCATION: (23)..(23)
<223> OTHER INFORMATION: FRET-component, preferably fluorescent dye

<400> SEQUENCE: 7
cacggtggag gtgaggcaga tgc                                              23

<210> SEQ ID NO 8
<211> LENGTH: 15
<212> TYPE: DNA
<213> ORGANISM: Artificial Sequence
<220> FEATURE:
<223> OTHER INFORMATION: real-time PCR probe specific for point mutation
      L858R of the EGFR gene (anchor probe)
<220> FEATURE:
<221> NAME/KEY: misc_binding
<222> LOCATION: (1)..(1)
<223> OTHER INFORMATION: FRET-component, preferably fluorescent dye

<400> SEQUENCE: 8
gtttggcccg cccaa                                                       15

<210> SEQ ID NO 9
<211> LENGTH: 30
<212> TYPE: DNA
<213> ORGANISM: Artificial Sequence
<220> FEATURE:
<223> OTHER INFORMATION: real-time PCR probe specific for point mutation
      L858R of the EGFR gene (anchor probe)
<220> FEATURE:
<221> NAME/KEY: misc_binding
<222> LOCATION: (30)..(30)
<223> OTHER INFORMATION: FRET-component, preferably fluorescent dye

<400> SEQUENCE: 9
gcatggtatt ctttctcttc cgcacccagc                                       30

<210> SEQ ID NO 10
<211> LENGTH: 14
<212> TYPE: DNA
<213> ORGANISM: Artificial Sequence
<220> FEATURE:
<223> OTHER INFORMATION: blocking agent according to the principle of
      locked nucleic acid applicable for real-time PCR specific for a
      region on the wild-type EGFR gene
<220> FEATURE:
<221> NAME/KEY: modified_base
<222> LOCATION: (1)..(14)
<223> OTHER INFORMATION: modification for the production of a blocking
      agent according to the principle of locked nucleic acid, whereby
      the C2 und C4 atome of the ribose/deoxyribose are linked via an
      oxygen methyl group

<400> SEQUENCE: 10
tgagctgcgt gatg                                                        14

<210> SEQ ID NO 11
<211> LENGTH: 15
<212> TYPE: DNA
<213> ORGANISM: Artificial Sequence
<220> FEATURE:
<223> OTHER INFORMATION: blocking agent according to the principle of
      locked nucleic acid applicable for real-time PCR specific for a
      region on the wild-type EGFR gene
```

```
<220> FEATURE:
<221> NAME/KEY: modified_BASE
<222> LOCATION: (1)..(15)
<223> OTHER INFORMATION: modification for the production of a blocking
      agent according to the principle of locked nucleic acid, whereby
      the C2 und C4 atome of the ribose/deoxyribose are linked via an
      oxygen methyl group

<400> SEQUENCE: 11
gccagcccaa aatct                                                      15
```